US012608805B2

(12) United States Patent
Washko, Jr. et al.

(10) Patent No.: US 12,608,805 B2
(45) Date of Patent: Apr. 21, 2026

(54) MACHINE LEARNING TO PREDICT LUNG CANCER INVOLVEMENT OF LYMPH NODES

(71) Applicant: Johnson & Johnson Enterprise Innovation Inc., New Brunswick, NJ (US)

(72) Inventors: George R. Washko, Jr., West Roxbury, MA (US); Raul San Jose Estepar, Wellesley, MA (US); Charles Matthew Kinsey, New Brunswick, NJ (US); Christopher Scott Stevenson, West Sussex (GB)

(73) Assignee: Johnson & Johnson Enterprise Innovation Inc., New Brunswick, NJ (US)

( * ) Notice: Subject to any disclaimer, the term of this patent is extended or adjusted under 35 U.S.C. 154(b) by 250 days.

(21) Appl. No.: 18/255,432

(22) PCT Filed: Nov. 30, 2021

(86) PCT No.: PCT/IB2021/061125
§ 371 (c)(1),
(2) Date: Jun. 1, 2023

(87) PCT Pub. No.: WO2022/118190
PCT Pub. Date: Jun. 9, 2022

(65) Prior Publication Data
US 2024/0005502 A1        Jan. 4, 2024

Related U.S. Application Data

(60) Provisional application No. 63/120,102, filed on Dec. 1, 2020.

(51) Int. Cl.
*G06T 7/00* (2017.01)
*G06V 10/764* (2022.01)
(Continued)

(52) U.S. Cl.
CPC .......... *G06T 7/0014* (2013.01); *G06V 10/764* (2022.01); *G06V 10/7715* (2022.01);
(Continued)

(58) Field of Classification Search
CPC ......... G06T 7/0014; G06T 2207/10068; G06T 2207/10081; G06T 2207/10088;
(Continued)

(56) References Cited

U.S. PATENT DOCUMENTS

2010/0057651 A1*   3/2010   Fung ........................ G06N 7/01
                                                          706/54
2011/0222751 A1*   9/2011   Barbu ..................... G06T 7/143
                                                          382/131
(Continued)

FOREIGN PATENT DOCUMENTS

CN          111340128 A   *   6/2020   ........... G06F 18/214
CN          111445946 A   *   7/2020   ........... G06F 18/241
(Continued)

OTHER PUBLICATIONS

Botta et al. "Association of a CT-Based Clinical and Radiomics Score of Non-Small Cell Lung Cancer (NSCLC) with Lymph Node Status and Overall Survival," 2020, Cancers, vol. 12, No. 6: 1432. https://doi.org/10.3390/cancers12061432 (Year: 2020).*
(Continued)

*Primary Examiner* — Emily C Terrell
*Assistant Examiner* — Julia Z. Yao
(74) *Attorney, Agent, or Firm* — Paradice & Li LLP

(57) ABSTRACT

Disclosed herein are methods for determining a subject level risk of metastatic cancer involving the training and/or deployment of models to determine 1) a lymph node level risk of individual lymph node involvement and/or 2) a subject level risk of lymph node involvement. Thus, the methods can identify patients who are high or low risk for
(Continued)

having nodal disease and optionally enable the guided intervention of cancer patients, for example, via treatment.

20 Claims, 30 Drawing Sheets

(51) Int. Cl.

| | |
|---|---|
| *G06V 10/77* | (2022.01) |
| *G06V 10/774* | (2022.01) |
| *G16H 30/40* | (2018.01) |
| *G16H 50/20* | (2018.01) |
| *G16H 50/30* | (2018.01) |

(52) U.S. Cl.
CPC ........... *G06V 10/774* (2022.01); *G16H 30/40* (2018.01); *G16H 50/20* (2018.01); *G16H 50/30* (2018.01); *G06T 2207/10068* (2013.01); *G06T 2207/10081* (2013.01); *G06T 2207/10088* (2013.01); *G06T 2207/10104* (2013.01); *G06T 2207/10116* (2013.01); *G06T 2207/10132* (2013.01); *G06T 2207/20064* (2013.01); *G06T 2207/20081* (2013.01); *G06T 2207/20084* (2013.01); *G06T 2207/30064* (2013.01); *G06T 2207/30096* (2013.01); *G06V 2201/03* (2022.01)

(58) Field of Classification Search
CPC . G06T 2207/10104; G06T 2207/10116; G06T 2207/10132; G06T 2207/20064; G06T 2207/20081; G06T 2207/20084; G06T 2207/30064; G06T 2207/30096; G06T 2207/20076; G06T 2207/30061; G06T 2207/30101; G06T 7/0012; G06V 10/764; G06V 10/7715; G06V 10/774; G06V 2201/03; G06V 10/25; G06V 10/40; G16H 30/40; G16H 50/20; G16H 50/30; G16H 50/50; G16H 20/00; G16H 30/00; G06N 3/09
See application file for complete search history.

(56) References Cited

U.S. PATENT DOCUMENTS

| | | | | |
|---|---|---|---|---|
| 2019/0019300 | A1* | 1/2019 | Simpson | ................... G06T 7/40 |
| 2019/0254611 | A1 | 8/2019 | Madabhushi et al. | |
| 2020/0085382 | A1* | 3/2020 | Taerum | ................ A61B 5/7264 |
| 2020/0193594 | A1 | 6/2020 | Georgescu et al. | |
| 2020/0245921 | A1 | 8/2020 | Li et al. | |
| 2020/0245960 | A1* | 8/2020 | Richter | ................ A61B 6/5205 |
| 2021/0003555 | A1* | 1/2021 | Ferte | ................... A61B 6/5217 |
| 2022/0028551 | A1* | 1/2022 | Jordan | ................... G16H 50/50 |
| 2022/0117544 | A1* | 4/2022 | Stavros | ................ A61B 5/0095 |
| 2022/0327690 | A1* | 10/2022 | Waterfield Price | .... G16H 50/20 |
| 2024/0242338 | A1* | 7/2024 | Lee | ........................... G06T 7/11 |

FOREIGN PATENT DOCUMENTS

| | | | | | |
|---|---|---|---|---|---|
| CN | 111584046 | A | * | 8/2020 | ............. G16H 30/40 |
| CN | 111862085 | A | * | 10/2020 | ............. G06N 3/045 |
| CN | 112530592 | A | * | 3/2021 | ........... G06T 7/0012 |
| EP | 1356421 | B1 | * | 12/2009 | ........... G06T 7/0012 |
| KR | 10-2010-0019057 | A | | 2/2010 | |
| KR | 20200120311 | A | * | 10/2020 | ............. G16H 50/20 |

OTHER PUBLICATIONS

Cong et al., "Development of a predictive radiomics model for lymph node metastases in pre-surgical CT-based stage IA non-small cell lung cancer," 2020, Lung Cancer, vol. 139, pp. 73-79. https://doi.org/10.1016/j.lungcan.2019.11.003 (Year: 2020).*

Keek et al. Computed tomography-derived radiomic signature of head and neck squamous cell carcinoma (peri)tumoral tissue for the prediction of locoregional recurrence and distant metastasis after concurrent chemo-radiotherapy. PLoS One. May 22, 2020;15(5):e0232639. doi: 10.1371/journal.pone.0232639. (Year: 2020).*

Yang et al. "A new approach to predict lymph node metastasis in solid lung adenocarcinoma: a radiomics nomogram," J Thorac Dis . Apr. 2018;10(Suppl 7): S807-S819. doi: 10.21037/jtd.2018. 03.126. PMID: 29780627; Pmcid: PMC5945690. (Year: 2018).*

Tosado et al. Clustering of Largely Right-Censored Oropharyngeal Head and Neck Cancer Patients for Discriminative Groupings to Improve Outcome Prediction. Sci Rep 10, 3811 (2020). https://doi.org/10.1038/s41598-020-60140-0 (Year: 2020).*

Peeken et al. A CT-based radiomics model to detect prostate cancer lymph node metastases in PSMA radioguided surgery patients . Eur J Nucl Med Mol Imaging 47, 2968-2977 (2020). https://doi.org/10.1007/s00259-020-04864-1 (Year: 2020).*

Debats et al. Lymph node detection in MR Lymphography: false positive reduction using multi-view convolutional neural networks. PeerJ. Nov. 22, 2019;7:e8052. doi: 10.7717/peerj.8052. PMID: 31772836; PMCID: PMC6876485. (Year: 2019).*

ISR and Written Opinion for International Patent Application No. PCT/IB2021/061125, dated Mar. 1, 2022 (16 pages).

Wang, et al., "Can peritumoral radiomics increase the efficiency of the prediction for lymph node metastasis in clinical stage T1 lung adenocarcinoma on CT?", Eur Radiol. Nov. 2019;29(11):6049-6058.

Office Action from Japanese Patent Application No. 2023-533338, dated Aug. 22, 2025, 17 pages.

\* cited by examiner

100

LoG
GLCM Feature Group

Wavelet
GLCM Feature Group

HLH_Imc2
HLL_Difference Entropy
HLL_SumEntropy
LLL_DifferenceEntropy
LLH_Imc2
HLL_Imc2
LLL_Imc2
LLL_Autocorrelation
LLL_SumAverage
LHL_MCC
LHH_MCC
HLH_Idn
LHH_Idn
LHH_SumAverage
LHH_DifferenceEntropy
LHH_DifferenceAverage
HHH_SumAverage
HHH_DifferenceEntropy
HLH_DifferenceAverage
LHL_SumAverage
HLH_DifferenceEntropy
LLH_DifferenceEntropy
LLH_SumEntropy
LLH_JointAverage

FIG. 5C

Wavelet
GLCM Feature Group

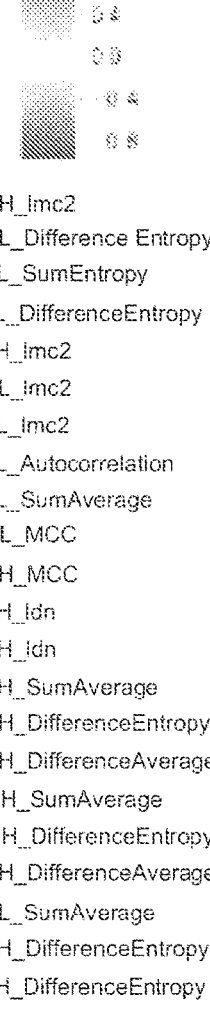

HLH_Imc2
HLL_Difference Entropy
HLL_SumEntropy
LLL_DifferenceEntropy
LLH_Imc2
HLL_Imc2
LLL_Imc2
LLL_Autocorrelation
LLL_SumAverage
LHL_MCC
LHH_MCC
HLH_Idn
LHH_Idn
LHH_SumAverage
LHH_DifferenceEntropy
LHH_DifferenceAverage
HHH_SumAverage
HHH_DifferenceEntropy
HLH_DifferenceAverage
LHL_SumAverage
HLH_DifferenceEntropy
LLH_DifferenceEntropy
LLH_SumEntropy
LLH_JointAverage LHH_Autocorrelation
LHH_SumSquares
LHH_DifferenceVariance
HHH_Contrast
HHH_SumSquares
HHH_DifferenceAverage
LLH_ClusterTendency
LLH_Contrast
HLH_Autocorrelation
HLH_SumSquares
HLH_DifferenceVariance
HLL_JointAverage
HLL_Autocorrelation
HLL_SumSquares
HLL_DifferenceVariance
LLL_ClusterTendency
LLL_Contrast
LHL_DifferenceAverage
LHL_SumAverage
HHL_DifferenceVariance
HHL_ClusterTendency
LHL_Autocorrelation
LHL_SumSquares
LHL_DifferenceVariance

FIG. 5D

Wavelet
GLCM Feature Group

HLH_Imc2
HLL_Difference Entropy
HLL_SumEntropy
LLL_DifferenceEntropy
LLH_Imc2
HLL_Imc2
LLL_Imc2
LLL_Autocorrelation
LLL_SumAverage
LHL_MCC
LHH_MCC
HLH_Idn
LHH_Idn
LHH_SumAverage
LHH_DifferenceEntropy
LHH_DifferenceAverage
HHH_SumAverage
HHH_DifferenceEntropy
HLH_DifferenceAverage
LHL_SumAverage
HLH_DifferenceEntropy
LLH_DifferenceEntropy
LLH_SumEntropy
LLH_JointAverage HHH_Idn
HHH_MCC
HHL_DifferenceEntropy
HHL_DifferenceAverage
HHL_SumAverage
LHH_Imc2
LHL_DifferenceEntropy
HHH_ClusterProminence
LHH_ClusterProminence
LLL_ClusterProminence
HHL_ClusterProminence
HLL_ClusterProminence
HLH_ClusterShade
LLL_Correlation
HHL_Correlation
HHH_Correlation
HLL_Correlation
LLH_Idn
LHL_Idmn
HHL_Idmn
HLL_Idmn
LLL_Idmn
LLH_InverseVariance
LLH_Imc1

FIG. 5E

Wavelet
GLCM Feature Group

HLH_Imc2
HLL_Difference Entropy
HLL_SumEntropy
LLL_DifferenceEntropy
LLH_Imc2
HLL_Imc2
LLL_Imc2
LLL_Autocorrelation
LLL_SumAverage
LHL_MCC
LHH_MCC
HLH_Idn
LHH_Idn
LHH_SumAverage
LHH_DifferenceEntropy
LHH_DifferenceAverage
HHH_SumAverage
HHH_DifferenceEntropy
HLH_DifferenceAverage
LHL_SumAverage
HLH_DifferenceEntropy
LLH_DifferenceEntropy
LLH_SumEntropy
LLH_JointAverage LHH_InverseVariance
HLL_ClusterShade
LHL_ClusterShade
LLH_MaximumProbability
HLH_Imc1
HLL_Id
LLL_Imc1
LLL_Id
LLH-Id
LHH_Id
LHH_JointEnergy
HHH_JointEnergy
HHH_Id
HLH_JointEnergy
HLH_Id
HHH_Imc1
LHL_Id
HHL_JointEnergy
HHL_InverseVariance
HHL_Idm
LLL_MaxProbability
LHL_MaxProbability
HLL_MaxProbability
LHL_Imc1

FIG. 5F

Wavelet
GLCM Feature Group

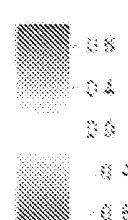

LHH_Autocorrelation
LHH_SumSquares
LHH_DifferenceVariance
HHH_Contrast
HHH_SumSquares
HHH_DifferenceAverage
LLH_ClusterTendency
LLH_Contrast
HLH_Autocorrelation
HLH_SumSquares
HLH_DifferenceVariance
HLL_JointAverage
HLL_Autocorrelation
HLL_SumSquares
HLL_DifferenceVariance
LLL_ClusterTendency
LLL_Contrast
LHL_DifferenceAverage
LHL_SumAverage
HHL_DifferenceVariance
HHL_ClusterTendency
LHL_Autocorrelation
LHL_SumSquares
LHL_DifferenceVariance HLH_Imc2
HLL_Difference Entropy
HLL_SumEntropy
LLL_DifferenceEntropy
LLH_Imc2
HLL_Imc2
LLL_Imc2
LLL_Autocorrelation
LLL_SumAverage
LHL_MCC
LHH_MCC
HLH_Idn
LHH_Idn
LHH_SumAverage
LHH_DifferenceEntropy
LHH_DifferenceAverage
HHH_SumAverage
HHH_DifferenceEntropy
HLH_DifferenceAverage
LHL_SumAverage
HLH_DifferenceEntropy
LLH_DifferenceEntropy
LLH_SumEntropy
LLH_JointAverage

FIG. 5G

Wavelet
GLCM Feature Group

LHH_Autocorrelation
LHH_SumSquares
LHH_DifferenceVariance
HHH_Contrast
HHH_SumSquares
HHH_DifferenceAverage
LLH_ClusterTendency
LLH_Contrast
HLH_Autocorrelation
HLH_SumSquares
HLH_DifferenceVariance
HLL_JointAverage
HLL_Autocorrelation
HLL_SumSquares
HLL_DifferenceVariance
LLL_ClusterTendency
LLL_Contrast
LHL_DifferenceAverage
LHL_SumAverage
HHL_DifferenceVariance
HHL_ClusterTendency
LHL_Autocorrelation
LHL_SumSquares
LHL_DifferenceVariance LHH_Autocorrelation
LHH_SumSquares
LHH_DifferenceVariance
HHH_Contrast
HHH_SumSquares
HHH_DifferenceAverage
LLH_ClusterTendency
LLH_Contrast
HLH_Autocorrelation
HLH_SumSquares
HLH_DifferenceVariance
HLL_JointAverage
HLL_Autocorrelation
HLL_SumSquares
HLL_DifferenceVariance
LLL_ClusterTendency
LLL_Contrast
LHL_DifferenceAverage
LHL_SumAverage
HHL_DifferenceVariance
HHL_ClusterTendency
LHL_Autocorrelation
LHL_SumSquares
LHL_DifferenceVariance

FIG. 5H

Wavelet
GLCM Feature Group

LHH_Autocorrelation
LHH_SumSquares
LHH_DifferenceVariance
HHH_Contrast
HHH_SumSquares
HHH_DifferenceAverage
LLH_ClusterTendency
LLH_Contrast
HLH_Autocorrelation
HLH_SumSquares
HLH_DifferenceVariance
HLL_JointAverage
HLL_Autocorrelation
HLL_SumSquares
HLL_DifferenceVariance
LLL_ClusterTendency
LLL_Contrast
LHL_DifferenceAverage
LHL_SumAverage
HHL_DifferenceVariance
HHL_ClusterTendency
LHL_Autocorrelation
LHL_SumSquares
LHL_DifferenceVariance LHH_InverseVariance
HLL_ClusterShade
LHL_ClusterShade
LLH_MaximumProbability
HLH_Imc1
HLL_Id
LLL_Imc1
LLL_Id
LLH_Id
LHH_Id
LHH_JointEnergy
HHH_JointEnergy
HHH_Id
HLH_JointEnergy
HLH_Id
HHH_Imc1
LHL_Id
HHL_JointEnergy
HHL_InverseVariance
HHL_Idm
LLL_MaxProbability
LHL_MaxProbability
HLL_MaxProbability
LHL_Imc1

FIG. 5J

Wavelet
GLCM Feature Group

HHH_Idn
HHH_MCC
HHL_DifferenceEntropy
HHL_DifferenceAverage
HHL_SumAverage
LHH_Imc2
LHL_DifferenceEntropy
HHH_ClusterProminence
LHH_ClusterProminence
LLL_ClusterProminence
HHL_ClusterProminence
HLL_ClusterProminence
HLH_ClusterShade
LLL_Correlation
HHL_Correlation
HHH_Correlation
HLL_Correlation
LLH_Idn
LHL_Idmn
HHL_Idmn
HLL_Idmn
LLL_Idmn
LLH_InverseVariance
LLH_Imc1

HLH_Imc2
HLL_Difference Entropy
HLL_SumEntropy
LLL_DifferenceEntropy
LLH_Imc2
HLL_Imc2
LLL_Imc2
LLL_Autocorrelation
LLL_SumAverage
LHL_MCC
HHH_MCC
HLH_Idn
LHH_Idn
LHH_SumAverage
LHH_DifferenceEntropy
LHH_DifferenceAverage
HHH_SumAverage
HHH_DifferenceEntropy
HLH_DifferenceAverage
LHL_SumAverage
HLH_DifferenceEntropy
LHL_DifferenceEntropy
LLH_SumEntropy
LLH_JointAverage

FIG. 5K

Wavelet
GLCM Feature Group

HHH_idn
HHH_MCC
HHL_DifferenceEntropy
HHL_DifferenceAverage
HHL_SumAverage
LHH_Imc2
LHL_DifferenceEntropy
HHH_ClusterProminence
LHH_ClusterProminence
LLL_ClusterProminence
HHL_ClusterProminence
HLL_ClusterProminence
HLH_ClusterShade
LLL_Correlation
HHL_Correlation
HHH_Correlation
HLL_Correlation
LLH_Idn
LHL_Idmn
HHL_Idmn
HLL_Idmn
LLL_Idmn
LLH_InverseVariance
LLH_Imc1

LHH_Autocorrelation
LHH_SumSquares
LHH_DifferenceVariance
HHH_Contrast
HHH_SumSquares
HHH_DifferenceAverage
LLH_ClusterTendency
LLH_Contrast
HLH_Autocorrelation
HLH_SumSquares
HLH_DifferenceVariance
HLL_JointAverage
HLL_Autocorrelation
HLL_SumSquares
HLL_DifferenceVariance
LLL_ClusterTendency
LLL_Contrast
LHL_DifferenceAverage
LHL_SumAverage
HHL_DifferenceVariance
HHL_ClusterTendency
LHL_Autocorrelation
LHL_SumSquares
LHL_DifferenceVariance

FIG. 5L

Wavelet
GLCM Feature Group

- HHH_idn
- HHH_MCC
- HHL_DifferenceEntropy
- HHL_DifferenceAverage
- HHL_SumAverage
- LHH_Imc2
- LHL_DifferenceEntropy
- HHH_ClusterProminence
- LHH_ClusterProminence
- LLL_ClusterProminence
- HHL_ClusterProminence
- HLL_ClusterProminence
- HLH_ClusterShade
- LLL_Correlation
- HHL_Correlation
- HHH_Correlation
- HLL_Correlation
- LLH_Idn
- LHL_Idmn
- HHL_Idmn
- HLL_Idmn
- LLL_Idmn
- LLH_InverseVariance
- LLH_Imc1

HHH_idn
HHH_MCC
HHL_DifferenceEntropy
HHL_DifferenceAverage
HHL_SumAverage
LHH_Imc2
LHL_DifferenceEntropy
HHH_ClusterProminence
LHH_ClusterProminence
LLL_ClusterProminence
HHL_ClusterProminence
HLL_ClusterProminence
HLH_ClusterShade
LLL_Correlation
HHL_Correlation
HHH_Correlation
HLL_Correlation
LLH_Idn
LHL_Idmn
HHL_Idmn
HLL_Idmn
LLL_Idmn
LLH_InverseVariance
LLH_Imc1

FIG. 5M

Wavelet
GLCM Feature Group

HHH_idn
HHH_MCC
HHL_DifferenceEntropy
HHL_DifferenceAverage
HHL_SumAverage
LHH_Imc2
LHL_DifferenceEntropy
HHH_ClusterProminence
LHH_ClusterProminence
LLL_ClusterProminence
HHL_ClusterProminence
HLL_ClusterProminence
HLH_ClusterShade
LLL_Correlation
HHL_Correlation
HHH_Correlation
HLL_Correlation
LLH_Idn
LHL_Idmn
HHL_Idmn
HLL_Idmn
LLL_Idmn
LLH_InverseVariance
LLH_Imc1

LHH_InverseVariance
HLL_ClusterShade
LHL_ClusterShade
LLH_MaximumProbability
HLH_Imc1
HLL_Id
LLL_Imc1
LLL_Id
LLH-Id
LHH_Id
LHH_JointEnergy
HHH_JointEnergy
HHH_Id
HLH_JointEnergy
HLH_Id
HHH_Imc1
LHL_Id
HHL_JointEnergy
HHL_InverseVariance
HHL_Idm
LLL_MaxProbability
LHL_MaxProbability
HLL_MaxProbability
LHL_Imc1

FIG. 5N

Wavelet
GLCM Feature Group

LHH_InverseVariance
HLL_ClusterShade
LHL_ClusterShade
LLH_MaximumProbability
HLH_Imc1
HLL_Id
LLL_Imc1
LLL_Id
LLH-Id
LHH_Id
LHH_JointEnergy
HHH_JointEnergy
HHH_Id
HLH_JointEnergy
HLH_Id
HHH_Imc1
LHL_Id
HHL_JointEnergy
HHL_InverseVariance
HHL_Idm
LLL_MaxProbability
LHL_MaxProbability
HLL_MaxProbability
LHL_Imc1

HLH_Imc2
HLL_Difference Entropy
HLL_SumEntropy
LLL_DifferenceEntropy
LLH_Imc2
HLL_Imc2
LLL_Imc2
LLL_Autocorrelation
LLL_SumAverage
LHL_MCC
LHH_MCC
HLH_Idn
LHH_Idn
LHH_SumAverage
LHH_DifferenceEntropy
LHH_DifferenceAverage
HHH_SumAverage
HHH_DifferenceEntropy
HLH_DifferenceAverage
LHL_SumAverage
HLH_DifferenceEntropy
LLH_DifferenceEntropy
LLH_SumEntropy
LLH_JointAverage

FIG. 5O

Wavelet
GLCM Feature Group

LHH_InverseVariance
HLL_ClusterShade
LHL_ClusterShade
LLH_MaximumProbability
HLH_Imc1
HLL_Id
LLL_Imc1
LLL_Id
LLH-Id
LHH_Id
LHH_JointEnergy
HHH_JointEnergy
HHH_Id
HLH_JointEnergy
HLH_Id
HHH_Imc1
LHL_Id
HHL_JointEnergy
HHL_InverseVariance
HHL_idm
LLL_MaxProbability
LHL_MaxProbability
HLL_MaxProbability
LHL_Imc1

LHH_Autocorrelation
LHH_SumSquares
LHH_DifferenceVariance
HHH_Contrast
HHH_SumSquares
HHH_DifferenceAverage
LLH_ClusterTendency
LLH_Contrast
HLH_Autocorrelation
HLH_SumSquares
HLH_DifferenceVariance
HLL_JointAverage
HLL_Autocorrelation
HLL_SumSquares
HLL_DifferenceVariance
LLL_ClusterTendency
LLL_Contrast
LHL_DifferenceAverage
LHL_SumAverage
HHL_DifferenceVariance
HHL_ClusterTendency
LHL_Autocorrelation
LHL_SumSquares
LHL_DifferenceVariance

FIG. 5P

Wavelet
GLCM Feature Group

LHH_InverseVariance
HLL_ClusterShade
LHL_ClusterShade
LLH_MaximumProbability
HLH_Imc1
HLL_Id
LLL_Imc1
LLL_Id
LLH-Id
LHH_Id
LHH_JointEnergy
HHH_JointEnergy
HHH_Id
HLH_JointEnergy
HLH_Id
HHH_Imc1
LHL_Id
HHL_JointEnergy
HHL_InverseVariance
HHL_Idm
LLL_MaxProbability
LHL_MaxProbability
HLL_MaxProbability
LHL_Imc1

HHH_idn
HHH_MCC
HHL_DifferenceEntropy
HHL_DifferenceAverage
HHL_SumAverage
LHH_Imc2
LHL_DifferenceEntropy
HHH_ClusterProminence
LHH_ClusterProminence
LLL_ClusterProminence
HHL_ClusterProminence
HLL_ClusterProminence
HLH_ClusterShade
LLL_Correlation
HHL_Correlation
HHH_Correlation
HLL_Correlation
LLH_idn
LHL_Idmn
HHL_Idmn
HLL_Idmn
LLL_Idmn
LLH_InverseVariance
LLH_Imc1

FIG. 5Q

Wavelet
GLCM Feature Group

LHH_InverseVariance
HLL_ClusterShade
LHL_ClusterShade
LLH_MaximumProbability
HLH_Imc1
HLL_Id
LLL_Imc1
LLL_Id
LLH-Id
LHH_Id
LHH_JointEnergy
HHH_JointEnergy
HHH_Id
HLH_JointEnergy
HLH_Id
HHH_Imc1
LHL_Id
HHL_JointEnergy
HHL_InverseVariance
HHL_Idm
LLL_MaxProbability
LHL_MaxProbability
HLL_MaxProbability
LHL_Imc1

LHH_InverseVariance
HLL_ClusterShade
LHL_ClusterShade
LLH_MaximumProbability
HLH_Imc1
HLL_Id
LLL_Imc1
LLL_Id
LLH-Id
LHH_Id
LHH_JointEnergy
HHH_JointEnergy
HHH_Id
HLH_JointEnergy
HLH_Id
HHH_Imc1
LHL_Id
HHL_JointEnergy
HHL_InverseVariance
HHL_Idm
LLL_MaxProbability
LHL_MaxProbability
HLL_MaxProbability
LHL_Imc1

FIG. 5R 50-50 split: LN level performance 50-50 split LN level performance

1

MACHINE LEARNING TO PREDICT LUNG CANCER INVOLVEMENT OF LYMPH NODES

CROSS REFERENCE TO RELATED APPLICATIONS

This application is the National Stage of International Patent Application No. PCT/IB2021/061125, which claims the benefit of and priority to U.S. Provisional Patent Application No. 63/120,102 filed Dec. 1, 2020, the entire disclosure of which is hereby incorporated by reference in its entirety for all purposes.

BACKGROUND

Computed tomographic (CT) imaging of the chest has become the clinical standard for the assessment of those at risk for lung cancer. These efforts are focused on the detection of lung nodules which may represent disease at its earliest and most curable stages. Detection of such a lung nodule triggers a more extensive clinical evaluation to determine if it is cancerous and if so, has it spread to other structures in the chest or even remote areas of the body. This is done to determine the stage of the lung cancer which in turn dictates the plan for therapeutic intervention.

One aspect of lung cancer staging is the determination of its presence or absence in the thoracic lymph nodes (nodal status). The current standard of care involves a staged approach where the nodule is first determined to be benign or malignant and then additional testing such as positron emission tomography (PET) scanning and surgical, endoscopic, or bronchoscopic based sampling of the lymph nodes is completed. Tissue sampling procedures add risk, expense and time to the work up. New, non-invasive methods are needed to mitigate these risks and shorten the time between diagnosis and treatment. As described in further detail herein, machine learning and deep learning-based techniques applied to the initial thoracic CT scan used for lung cancer screening can address these needs.

Lung cancer detection, staging and treatment planning is a multistep process that can take weeks or months. In addition to the risk and expense of such a clinical work up, the extra time necessitated by this process leads to significant patient anxiety and heightened chances of interval metastases. In fact, longer diagnosis to treatment times are associated with a worse overall survival. An exemplary approach to mitigating these concerns is one that allows near simultaneous cancer diagnosis, staging and in the case of bronchoscopic approaches to therapy, treatment.

SUMMARY

Embodiments of the invention disclosed herein are based upon analysis of thoracic CT scans used to screen for lung cancer in high risk populations. In some aspects, it identifies patients at high risk for cancer that has metastasized to at least one lymph node (LN) in the chest and therefore require additional testing such as PET scanning and lymph node biopsy. This allows the clinical providers to prioritize testing to those at greatest need. Conversely, patients with suspected lung cancer who are at low risk for having lymph node metastasis could proceed directly to immediate therapy such as surgical resection or combined bronchoscopic diagnosis and treatment. This will eliminate the time between disease diagnosis and therapy. Specifically, embodiments of the invention disclosed herein enable identification of patients who are high or low risk for having nodal disease thereby allowing clinicians to either prioritize additional testing in high risk individuals or have lung cancer patients with low metastatic risk proceed directly to confirmatory bronchoscopic biopsy immediately followed by bronchoscopically delivered therapy.

Disclosed herein is a method of determining a subject level risk of metastatic cancer of a subject, the method comprising: obtaining one or more images captured from the subject comprising a plurality of lymph nodes of the subject; and predicting the subject level risk of metastatic cancer by applying a risk model to extracted features of the obtained one or more images, the risk model trained to predict lymph node (LN) level risks of metastatic cancer for lymph nodes in images, wherein the risk model is trained using at least labels derived from imputed LN-level risks of metastatic cancer for a set of lymph nodes of a reference individual, the imputed LN-level risks of the set of lymph nodes determined using at least an imputation model that discriminates between cancerous and non-cancerous lymph nodes of training images. In various embodiments, predicting the subject level risk of metastatic cancer further comprises: selecting one or more of the plurality of lymph nodes based on their LN-level risk of metastatic cancer predicted by the risk model; and determining the subject level risk of metastatic cancer using the LN-level risk of metastatic cancer predicted for the one or more lymph nodes.

In various embodiments, selecting one or more of the plurality of lymph nodes comprises identifying the lymph node with the highest probability of LN-level risk, and wherein determining the subject level risk of metastatic cancer comprises assigning the highest probability of LN-level risk as the subject level risk of metastatic cancer. In various embodiments, the risk model predicts LN-level risks of metastatic cancer with a greater range of probabilities than the imputed LN-level risks predicted by the imputation model. In various embodiments, the set of lymph nodes of a reference individual is selected by: determining a median risk value; and comparing imputed LN-level risks of the lymph nodes of the reference individual to the median risk value. In various embodiments, the set of lymph nodes of a reference individual is further selected by: including one or more lymph nodes with LN-level risks greater than the median risk value in the set of lymph nodes. In various embodiments, one or more lymph nodes with LN-level risks less than the median risk value in the set of lymph nodes are excluded from the set of lymph nodes.

In various embodiments, the median risk value is a median intrasubject LN-level risk of the reference individual. In various embodiments, the one or more images comprises a computed tomography (CT) image. In various embodiments, the one or more images comprises are obtained from a thoracic CT scan. In various embodiments, methods disclosed herein further comprise determining a stage of the cancer according to the predicted subject level risk of metastatic cancer. In various embodiments, methods disclosed herein further comprise selecting a diagnostic or treatment for the subject according to the predicted subject level risk of metastatic cancer. In various embodiments, selecting a diagnostic or treatment for the subject comprises selecting either surgical tumor resection or combined bronchoscopic or endoscopic diagnosis and treatment when the predicted subject level risk of metastatic cancer is below a threshold risk value. In various embodiments, selecting a diagnostic or treatment for the subject comprises selecting additional diagnostic testing of one or both of performing a PET or PET-CT scan or performing a lymph node biopsy when the predicted subject level risk of metastatic cancer is above a threshold risk value.

In various embodiments, the imputation model is trained using training images obtained from thoracic CT scans. In various embodiments, the training images obtained from thoracic CT scans comprise one or more lymph nodes. In various embodiments, the imputation model is trained using training images of the National Lung Screening Trial (NLST). In various embodiments, the imputation model is trained using training images of a custom dataset.

In various embodiments, the imputation model is trained by generating two or more radiomic panels from at least one of the training images. In various embodiments, the two or more radiomic panels comprise a Laplacian of Gaussians transformation of the training image and a wavelet transform of the training image. In various embodiments, the imputation model is further trained by extracting features from each of the two or more radiomic panels; and training the imputation model using at least the extracted features. In various embodiments, the imputation model is further trained by: defining a region of interest (ROI) in the radiomic panels, the defined region of interest comprising a lymph node; extracting features from the ROI in the radiomic panels; and training the imputation model using at least the extracted features. In various embodiments, the extracted features include one or more feature categories of first order features, shape features, gray level co-occurrence matrix 1 (GLCM) features, gray level run length matrix (GLRLM) features, gray level size zone matrix (GLSZM) features, and neighborhood gray tone difference matrix (NGTDM) features.

In various embodiments, the imputation model is further trained using reference ground truth values indicating a presence or absence of metastasis in training images. In various embodiments, the reference ground truth values are derived from Nstage covariable values indicating the stage of the cancer, wherein a cancer stage of "0" or "1" indicate an absence of metastasis and wherein a cancer stage of "2" or "3" indicate a presence of metastasis. In various embodiments, the reference ground truth values indicate whether individual lymph nodes are cancerous or non-cancerous. In various embodiments, the reference ground truth values indicating whether individual lymph nodes are cancerous or non-cancerous are back-calculated from the Nstage covariable values based on characteristics of the tumor or lymph nodes.

In various embodiments, the imputation model is a random forest classifier or a LASSO classifier. In various embodiments, the risk model is a random forest classifier or a LASSO classifier. In various embodiments, the risk model is trained using supervised learning techniques. In various embodiments, the plurality of lymph nodes comprises 1, 2, 3, 4, 5, 6, 7, 8, 9, 10, 11, 12, 13, 14, 15, 16, 17, 18, 19, 20, or 21 lymph nodes. In various embodiments, the plurality of lymph nodes comprises between 8 to 20 lymph nodes, between 10 to 19 lymph nodes, between 12 to 18 lymph nodes, or between 14 and 16 lymph nodes. In various embodiments, the metastatic cancer is metastatic lung cancer. In various embodiments, the risk model exhibits a performance of at least AUC=78%, Sensitivity=82%, or Specificity=60%.

Additionally disclosed herein is a method of training the risk model of any one of the claims herein, the method comprising: applying an imputation model to generate imputed LN-level risks for a plurality of lymph nodes in training images; selecting a set of lymph nodes, wherein the lymph nodes in the set have LN-level risks that are greater than a median risk value; using the LN-level risks of the lymph nodes in the set of lymph nodes as reference ground truths for training the risk model, the risk model able to predict LN-level risks with a greater range of probabilities than the imputed LN-level risks predicted by the imputation model. In various embodiments, the risk model is further trained by extracting features from one or more radiomic panels; and training the risk model using at least the extracted features. In various embodiments, extracting features from two or more radiomic panels comprises: defining a region of interest (ROI) in the one or more radiomic panels, the defined region of interest comprising a lymph node; extracting features from the ROI in the one or more radiomic panels. In various embodiments, the extracted features include one or more feature categories of first order features, shape features, gray level co-occurrence matrix 1 (GLCM) features, gray level run length matrix (GLRLM) features, gray level size zone matrix (GLSZM) features, and neighborhood gray tone difference matrix (NGTDM) features.

Additionally disclosed herein is a system for performing the methods described above. In various embodiments, a system for determining a subject level risk of metastatic cancer of a subject comprises: an imaging device configured to capture one or more images of the subject; and a computing device configured to perform the steps of: obtaining one or more images captured from the subject comprising a plurality of lymph nodes of the subject; and predicting the subject level risk of metastatic cancer by applying a risk model to extracted features of the obtained one or more images, the risk model trained to predict lymph node (LN) level risks of metastatic cancer for lymph nodes in images, wherein the risk model is trained using at least labels derived from imputed LN-level risks of metastatic cancer for a set of lymph nodes of a reference individual, the imputed LN-level risks of the set of lymph nodes determined using at least an imputation model that discriminates between cancerous and non-cancerous lymph nodes of training images.

Additionally disclosed herein is a non-transitory computer readable mediums for performing the method described above. In various embodiments, a non-transitory computer readable medium comprises instructions that, when executed by a processor, cause the processor to: obtain one or more images captured from the subject comprising a plurality of lymph nodes of the subject; and predict the subject level risk of metastatic cancer by applying a risk model to extracted features of the obtained one or more images, the risk model trained to predict lymph node (LN) level risks of metastatic cancer for lymph nodes in images, wherein the risk model is trained using at least labels derived from imputed LN-level risks of metastatic cancer for a set of lymph nodes of a reference individual, the imputed LN-level risks of the set of lymph nodes determined using at least an imputation model that discriminates between cancerous and non-cancerous lymph nodes of training images.

BRIEF DESCRIPTION OF THE DRAWINGS

These and other features, aspects, and advantages of the present invention will become better understood with regard to the following description and accompanying drawings.

Figure 1A:
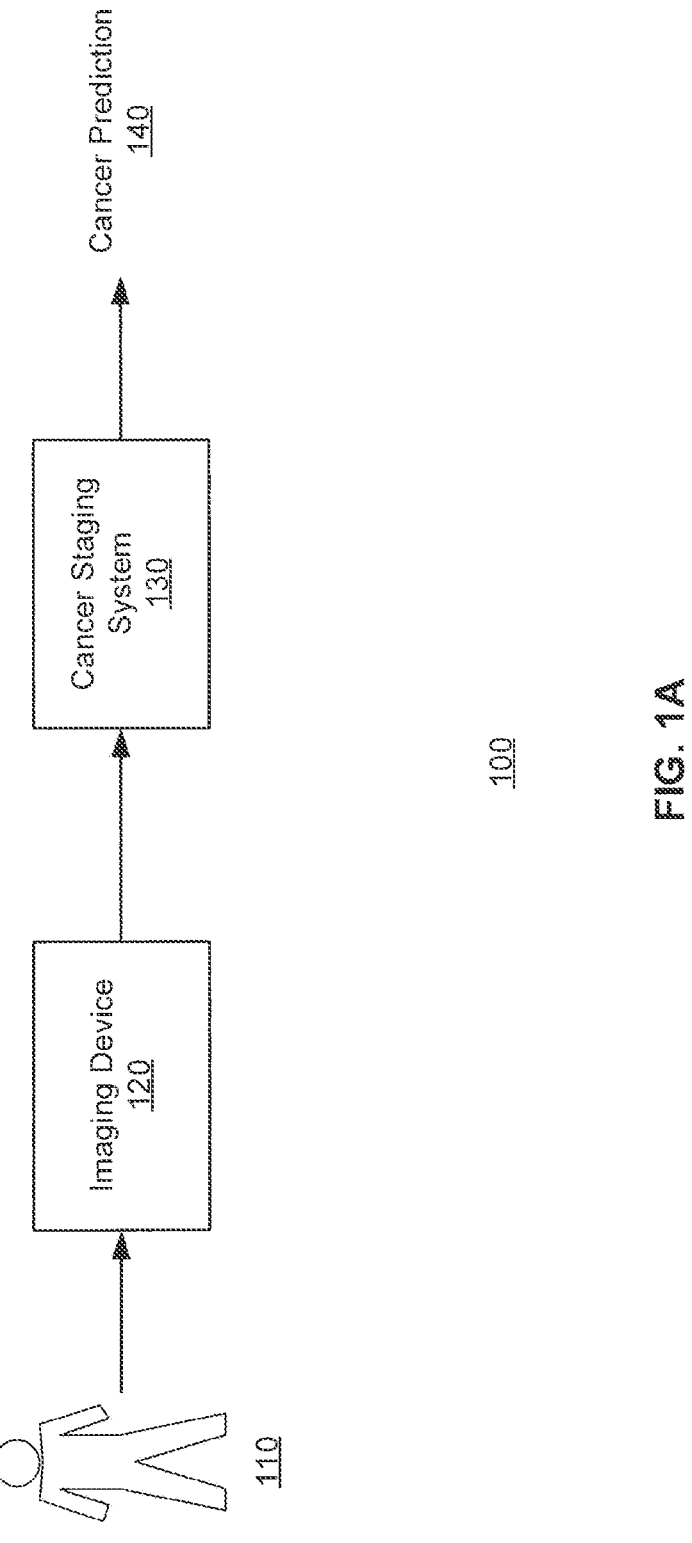
FIG. 1A depicts a system environment overview for cancer staging by determining a subject level risk of metastatic cancer of a subject, in accordance with an embodiment.

It is noted that wherever practicable similar or like reference numbers may be used in the figures and may indicate similar or like functionality. For example, a letter after a reference numeral, such as "individual 315A," indicates that the text refers specifically to the element having that particular reference numeral. A reference numeral in the text without a following letter, such as "individual 315," refers to any or all of the elements in the figures bearing that reference numeral (e.g. "individual 315" in the text refers to reference numerals "individual 315A," "individual 315B," "individual 315C," and "individual 315D" in the figures).

DETAILED DESCRIPTION

I. Definitions

Terms used in the claims and specification are defined as set forth below unless otherwise specified.

The term "subject" encompasses a cell, tissue, or organism, human or non-human, whether in vivo, ex vivo, or in vitro, male or female.

The term "mammal" encompasses both humans and non-humans and includes but is not limited to humans, non-human primates, canines, felines, murines, bovines, equines, and porcines.

The term "sample" of "test sample" can include a single cell or multiple cells or fragments of cells or an aliquot of body fluid, such as a blood sample, taken from a subject, by means including venipuncture, excretion, ejaculation, massage, biopsy, needle aspirate, lavage sample, scraping, surgical incision, or intervention or other means known in the art. Examples of an aliquot of body fluid include amniotic fluid, aqueous humor, bile, lymph, breast milk, interstitial fluid, blood, blood plasma, cerumen (earwax), Cowper's fluid (pre-ejaculatory fluid), chyle, chyme, female ejaculate, menses, mucus, saliva, urine, vomit, tears, vaginal lubrication, sweat, serum, semen, sebum, pus, pleural fluid, cerebrospinal fluid, synovial fluid, intracellular fluid, and vitreous humour.

The term "reference individual" refers to an individual with known cancer staging. For example, reference individuals can include healthy individuals (e.g., control individuals). As another example, reference individuals can include individuals previously diagnosed with cancer and staged. As another example, reference individuals include individuals previously diagnosed with cancer that has metastasized to the lymph nodes, e.g., stage IV cancer.

The term "obtaining one or more images" encompasses obtaining one or more images captured from a subject or obtaining one or more images captured from a sample obtained from a subject. Obtaining one or more images can encompass performing steps of capturing the one or more images from the subject or from a sample obtained from the subject. The phrase can also encompass receiving one or more images, e.g., from a third party that has performed the steps of capturing the one or more images from the subject or from a sample obtained from the subject. The one or more images can be obtained by one of skill in the art via a variety of known ways including stored on a storage memory.

The terms "lymph node involvement," "lymph node metastasis," or "lymph node cancer" refer to the presence or absence of metastasized cancer in one or more lymph nodes of a subject.

The terms "lymph node metastatic risk," "lymph node level risk," and "LN-level risk" are used interchangeably and generally refer to a risk of metastatic cancer in a specific lymph node.

The phrase "subject level risk of metastatic cancer" or "patient level risk of metastatic cancer" are used interchangeably and refer to a likelihood that a cancer in a subject has metastasized. In various embodiments, the cancer in the subject is a lung cancer that has metastasized in one or more lymph nodes of the subject.

The term "cancer stage" or "stage of cancer" refers to a stage of a cancer in a subject. Cancer stage can refer to the TNM staging system which includes stages 0-4. Additionally, cancer stage can refer to nodal cancer stages 0-3. Nodal cancer stage 0 indicates no nodal involvement, nodal cancer stage 1 indicates hilar nodal involvement, and nodal stages 2 or 3 indicate mediastinal involvement.

It must be noted that, as used in the specification, the singular forms "a," "an" and "the" include plural referents unless the context clearly dictates otherwise.

II. System Environment Overview

FIG. 1A depicts a system environment overview 100 for cancer staging by determining a subject level risk of metastatic cancer of a subject, in accordance with an embodiment. The system environment 100 provides context in order to introduce a subject 110, an imaging device 120, and a cancer staging system 130 for determining a cancer prediction 140. In various embodiments, the cancer prediction 140 determined by the cancer staging system 130 serves as the cancer staging for the subject 110. In various embodiments, the cancer prediction 140 determined by the cancer staging system 130 is a predicted level of risk for the subject 110 and serves as a basis for determining a cancer staging for the subject 110.

In various embodiments, the subject is healthy. Thus, the methods for cancer staging described herein can be beneficial for early detection of cancer in the healthy subject. In various embodiments, the subject was previously diagnosed with a cancer. In various embodiments, the subject is healthy, but is suspected to have a form of cancer (e.g., a subject who has exhibited symptoms associated with a cancer). In particular embodiments, the type of cancer in the subject is a lung cancer. Thus, the methods for cancer staging described herein can be beneficial for identifying and differentiating subjects who are at high risk of metastatic cancer including lymph node involvement and subjects with suspected lung cancer who are at low risk for having lymph node metastasis. Subjects at high risk of metastatic cancer can undergo additional testing such as PET scanning and lymph node biopsy whereas subjects who are at low risk for having lymph node metastasis can undergo immediate therapy such as surgical resection of the lung cancer or combined bronchoscopic diagnosis and treatment.

In various embodiments, the imaging device 120 captures an image from the subject 110 for further analysis. In various embodiments, the imaging device 120 captures an image from a test sample obtained from the subject 110. The image and/or the sample can be obtained by the individual or by a third party, e.g., a health care provider or a medical professional. Examples of medical professionals include physicians, emergency medical technicians, nurses, first responders, psychologists, phlebotomist, medical physics personnel, nurse practitioners, surgeons, dentists, and any other obvious medical professional as would be known to one skilled in the art.

In some embodiments, the imaging device 120 captures an image of an anatomical location of the subject 110. Example anatomical locations of a subject can include lungs, thoracic cavity, kidney, liver, pancreas, brain, stomach, intestines, hip, knees, legs, arms, and face. In various embodiments, the imaging device 120 captures an image of the thoracic cavity of the subject 110. In various embodiments, the imaging device 120 captures an image of one or more lymph nodes of the subject 110. In various embodiments, the imaging device 120 captures an image of the thoracic cavity including one or more lymph nodes of the subject 110.

In various embodiments, the imaging device 120 is one of a computed tomography (CT) scanner, magnetic resonance imaging (MRI) scanner, positron emission tomography (PET) scanner, x-ray scanner, or an ultrasound imaging device. In particular embodiments, the imaging device 120 is a CT scanner that captures one or more images of the subject 110. In particular embodiments, the imaging device 120 is a CT scanner that captures one or more CT images of the thoracic cavity including one or more lymph nodes of the subject 110.

Generally, the cancer staging system 130 analyzes one or more images (e.g., images captured by the imaging device 120) and generates the cancer prediction 140. In various embodiments, the cancer prediction 140 can be a predicted stage of cancer in the subject 110. In various embodiments, the cancer prediction 140 can be a predicted likelihood of cancer lymph node involvement in the subject 110. In various embodiments, the cancer prediction 140 can include a recommended clinical approach (e.g., additional testing such as PET scanning and lymph node biopsy) or therapy (e.g., surgical resection and/or drug therapy). The cancer staging system 130 can include one or more computers, embodied as a computer system 400 as discussed below with respect to FIG. 4. Therefore, in various embodiments, the steps described in reference to the cancer staging system 130 are performed in silico.

In various embodiments, the imaging device 120 and the cancer staging system 130 are employed by different parties. For example, a first party operates the imaging device 120 120 to capture one or more images from the subject 110 and then provides the captured one or more images to a second party which implements the cancer staging system 130 to determine a cancer prediction 140.

Figure 1B:
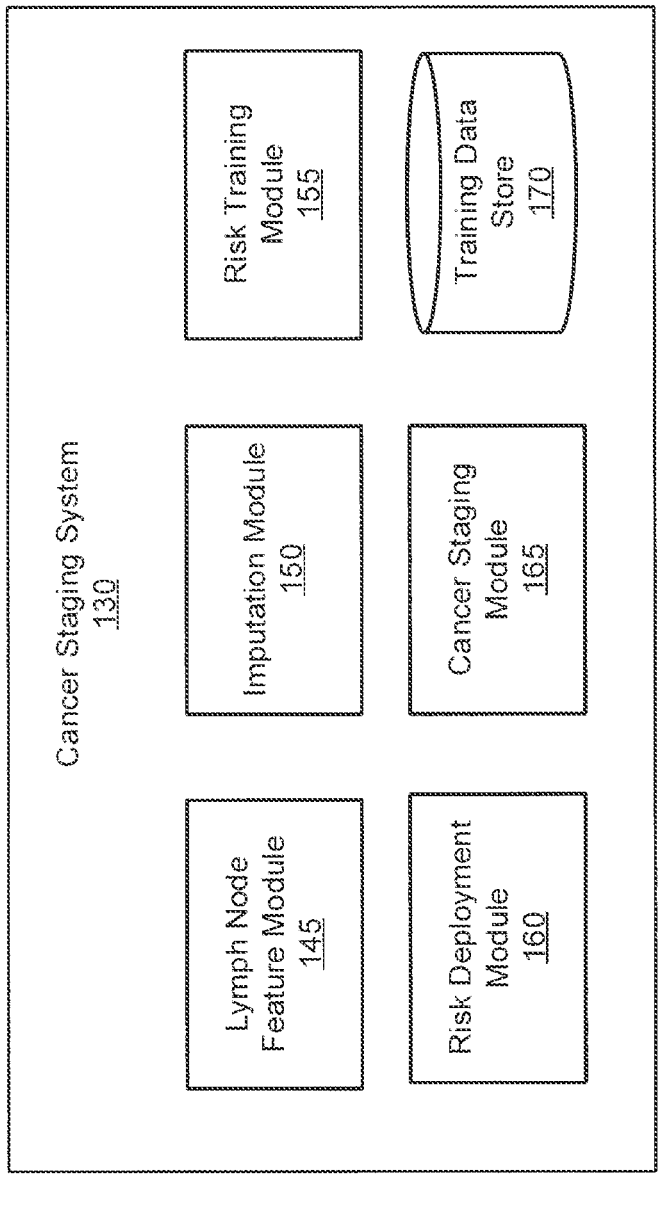
FIG. 1B depicts a block diagram of the cancer staging system, in accordance with an embodiment.

Reference is now made to FIG. 1B which depicts a block diagram illustrating the computer logic components of the cancer staging system 130, in accordance with an embodiment. Specifically, the cancer staging system 130 may include a lymph node feature module 145, an imputation module 150, a risk training module 155, a risk deployment module 160, a cancer prediction module 165, and a training data store 170.

Generally, the lymph node feature module 145 extracts features from images derived from subjects or training subjects. The imputation module 150 trains and deploys an imputation model. The imputation model analyzes extracted features and determines lymph node level risk of cancer for each lymph node in images. The risk training module 155 trains a risk model using training data including at least the lymph node level risk of cancer determined by the imputation model. The risk deployment module 160 implements the risk model to analyze features extracted from images obtained from a subject (e.g., subject 110 in FIG. 1A) to determine a cancer prediction, such as a prediction of subject level metastatic risk or a cancer stage, for the subject 110. Put another way, the cancer staging system 130 trains and implements at least two models (e.g., an imputation model and a risk model). Thus, through this multi-step implementation that involves the at least two models, the cancer staging system 130 generates a cancer prediction, such as subject level metastatic risk or a prediction of a cancer stage, for a subject.

The implementation of both the imputation model and the risk model results in an improved cancer prediction. Specifically, the imputation model learns from the subject-level N-stage of the training data and is applied to features extracted of the lymph nodes to define which lymph nodes are likely to contribute to a positive N-stage. Then, the risk model learns a more refined lymph node metastatic risk probability from the imputed data. Here, the risk model predicts LN-level risks of metastatic cancer with a greater range of probabilities than the imputed LN-level risks predicted by the imputation model. This enables a more accurate determination of subject level risk of metastatic cancer.

The components of the cancer staging system 130 are hereafter described in reference to two phases: 1) a training phase and 2) a deployment phase. More specifically, the training phase refers to the building and training of one or more models based on training data, such as training images captured from reference individuals (e.g., individuals with a known cancer staging). Therefore, the models are trained using the training data such that during the deployment phase, implementation of the models enables the prediction of a cancer staging for a subject (e.g., subject 110 in FIG. 1A). In various embodiments, the imputation module 150 can also be implemented to train and deploy a model, hereafter referred to as an imputation model. Thus, the imputation module 150 trains the imputation model during the training phase and deploys the imputation model during the deployment phase.

In some embodiments, the components of the cancer staging system 130 are applied during one of the training phase and the deployment phase. For example, the risk training module 155 and training data store 170 are applied during the training phase to train a risk model. Additionally, the risk deployment module 160 is applied during the deployment phase. In various embodiments, the components of the cancer staging system 130 can be performed by different parties depending on whether the components are applied during the training phase or the deployment phase. In such scenarios, the training and deployment of the prediction model are performed by different parties. For example, the risk training module 155 and training data store 170 applied during the training phase can be employed by a first party (e.g., to train a risk model) and the risk deployment module 160 applied during the deployment phase can be performed by a second party (e.g., to deploy the risk model). Similarly, the imputation module 150 can be applied to train an imputation model by a first party and the imputation module 150 can be applied to deploy an imputation model by a second party.

III. Methods for Cancer Staging

Embodiments described herein include methods for cancer staging by analyzing one or more images captured from a subject and applying one or more models to determine a subject level of metastatic cancer risk involving the lymph nodes. Such methods can be performed by the cancer staging system 130 described in FIG. 1B.

Referring to the modules of the cancer staging system 130 in FIG. 1B, the lymph node feature module 145 analyzes one or more images and extracts features from the one or more images. In various embodiments, the lymph node feature module 145 extracts features from training images obtained from reference individuals. These features extracted from training images can be used to train one or more models, such as an imputation model, as is described in further detail below. In various embodiments, the lymph node feature module 145 extracts features images obtained from a subject (e.g., subject 110 in FIG. 1A). These features extracted from images obtained from the subject can be analyzed by deploying a model, such as a risk model, as is described in further detail below.

In various embodiments, the one or more images or training images includes one or more lymph nodes in the image. For example, the image or training image can be an image of a thoracic cavity including one or more lymph nodes. In various embodiments, an image includes at least 2 lymph nodes. In various embodiments, an image includes 1, 2, 3, 4, 5, 6, 7, 8, 9, 10, 11, 12, 13, 14, 15, 16, 17, 18, 19, 20, or 21 lymph nodes. In various embodiments, an image includes between 1-10 lymph nodes, 1-15 lymph nodes, 2-10 lymph nodes, 2-15 lymph nodes, 2-20 lymph nodes, 4-10 lymph nodes, 4-15 lymph nodes, 4-20 lymph nodes, 5-10 lymph nodes, 5-15 lymph nodes, 5-20 lymph nodes, 8-15 lymph nodes, 8-20 lymph nodes, 10-15 lymph nodes, 10-20 lymph nodes, 12-15 lymph nodes, 12-20 lymph nodes, or 15-20 lymph nodes. In various embodiments, multiple images are captured from a single subject or a reference individual. The multiple images can capture different lymph nodes of a subject or reference individual. In various embodiments, the multiple images include at least 2 lymph nodes. In various embodiments, the multiple images include 2, 3, 4, 5, 6, 7, 8, 9, 10, 11, 12, 13, 14, 15, 16, 17, 18, 19, 20, or 21 lymph nodes. In various embodiments, the multiple images include between 8 to 20 lymph nodes. In various embodiments, the multiple images include between 10 to 19 lymph nodes, between 12 to 18 lymph nodes, or between 14 and 16 lymph nodes.

Figure 2B:
FIG. 2B is an example lymph node annotation, in accordance with an embodiment.
Figure 2A:
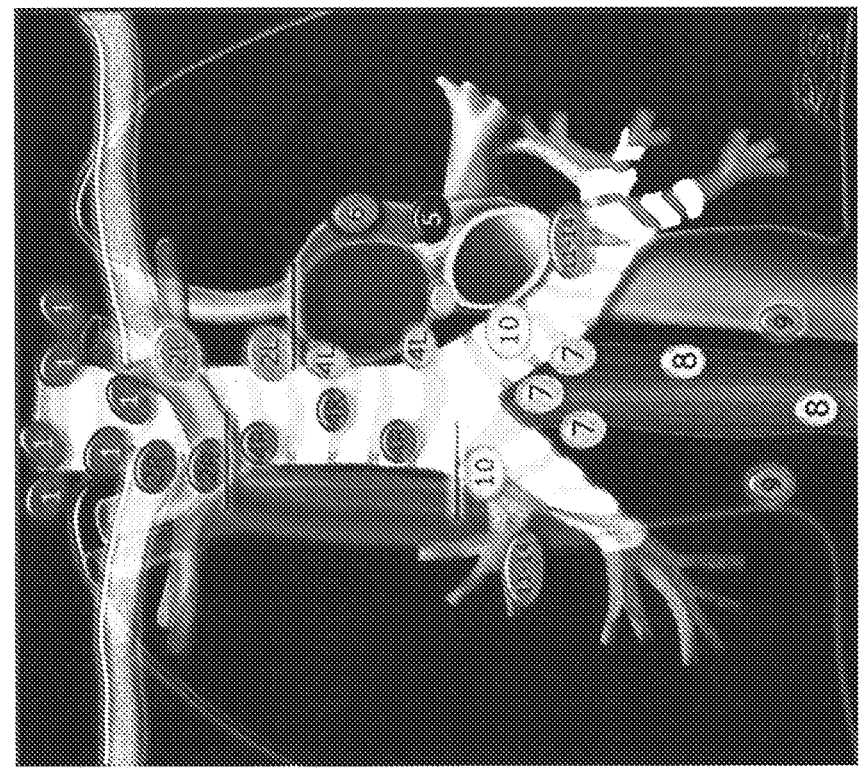
FIG. 2A depicts an example lymph node map identifying lymph node stations, in accordance with an embodiment.

FIG. 2A depicts an example lymph node map identifying lymph node stations, in accordance with an embodiment. More specifically, FIG. 2A is a depiction of regional lymph node classifications adapted from the American Thoracic Society mapping scheme. Here, lymph node stations are annotated to depict the location and categorization of each lymph node. Specifically, the annotations are as follows: (1) Supraclavicular nodes, (2R/2L) Upper paratracheal nodes, (3A) Pre-vascular nodes, (3P) Pre-vertebral nodes, (4R/4L) Lower Paratracheal nodes, (5) Subaortic nodes, (6) para-aortic nodes, (7) subcarinal nodes, (8) paraesophageal nodes, (9) pulmonary ligament nodes, (10) Hilar nodes, (11)

interlobar nodes, (12) lobar nodes, (13) segmental nodes, and (14) sub-segmental nodes).

The lymph node feature module 145 annotates one or more lymph nodes in the image. In various embodiments, the lymph node feature module 145 annotates one or more lymph nodes by defining a region around the lymph node. In various embodiments, the defined region around the lymph node is a spherical region. In various embodiments, the spherical region has a radius of X mm. In various embodiments, X is 5 mm. In various embodiments, X is 7.5 mm. In some embodiments, X is 0.5 mm, 1 mm, 1.5 mm, 2 mm, 2.5 mm, 3 mm, 3.5 mm, 4 mm, 4.5 mm, 5.5 mm, 6 mm, 6.5 mm, 7 mm, 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, or 15 mm. In various embodiments, X is between 1 and 15 mm. In various embodiments, X is between 2 and 12 mm. In various embodiments, X is between 3 and 10 mm. In various embodiments, X is between 4 and 8 mm. In various embodiments, X is between 5 and 7.5 mm. In various embodiments, X is between 4 and 6 mm. In various embodiments, X is between 6 and 8 mm. In various embodiments, X is between 7 and 8 mm. In various embodiments, X is between 10 and 15 mm.

In various embodiments, the lymph node feature module 145 annotates one or more lymph nodes by defining two or more spherical regions around lymph nodes. For example, the lymph node feature module 145 annotates one or more lymph nodes by defining a first spherical region of 5 mm around the lymph node and a second spherical region of 7.5 mm around the lymph node. FIG. 2B is an example lymph node annotation, in accordance with an embodiment. Specifically, FIG. 2B depicts two defined spherical regions around two 2R upper paratracheal nodes.

In various embodiments, the lymph node feature module 145 extracts features from each defined region around a lymph node. In various embodiments, the lymph node feature module 145 performs a transformation of the original input to generate a transformed image from which additional features are then extracted. In one embodiment, the lymph node feature module 145 performs a wavelet transform of the original image. In one embodiment, the lymph node feature module 145 performs a Laplacian of Gaussians (LoG) of the original image. Therefore, the lymph node feature module 145 can extract features from defined regions around lymph nodes in the transformed image. In various embodiments, the lymph node feature module 145 extracts features from defined regions around lymph nodes in the original image and the transformed image.

In particular embodiments, the lymph node feature module 145 performs two transforms of the original image (e.g., both a wavelet transform of the original image and a Laplacian of Gaussians (LoG) of the original image). Thus, the lymph node feature module 145 can extract features from defined regions around lymph nodes in both the first transformed image and the second transformed image. In various embodiments, the lymph node feature module 145 extracts features from defined regions around lymph nodes in the original image, the first transformed image, and the second transformed image.

Example feature categories from the original image, the first transformed image, and/or the second transformed image can include first order features, shape features, gray level co-occurrence matrix 1 (GLCM) features, gray level run length matrix (GLRLM) features, gray level size zone matrix (GLSZM) features, and neighborhood gray tone difference matrix (NGTDM) features. First order features refer to features of the first-order statistics of the intensity values. GLCM features derive from a histogram of co-occurring greyscale values at a given offset over an image. GLRLM features involve statistics of the gray level run length matrix. GLSZM features involve statistics of the gray level size zone matrix. NGTDM features involve statistics of the neighboring gray tone difference matrix. Examples of features in the different feature categories include correlation features, LMC2, MCC, Difference in Entropy, Joint Entropy, Sum of Entropy, Cluster prominence, average difference, joint average, sum of average, autocorrelation, difference in variance, contrast, cluster tendency, sum of squares, LDMN, LDN, Cluster shade, LMC1, Inverse variance, LD, LDM, joint energy, and maximum probability.

In various embodiments, the lymph node feature module 145 extracts at least 50 features from an image. In various embodiments, the lymph node feature module 145 extracts at least 100 features, at least 150 features, at least 200 features, at least 250 features, at least 300 features, at least 350 features, at least 400 features, at least 450 features, at least 500 features, at least 550 features, at least 600 features, at least 650 features, at least 700 features, at least 750 features, at least 800 features, at least 850 features, at least 900 features, at least 950 features, at least 1000 features, at least 1100 features, at least 1200 features, at least 1300 features, at least 1400 features, at least 1500 features, at least 1600 features, at least 1700 features, at least 1800 features, at least 1900 features, at least 2000 features, at least 3000 features, at least 4000 features, at least 5000 features, at least 6000 features, at least 7000 features, at least 8000 features, at least 9000 features, or at least 10,000 features from an image. In various embodiments, the lymph node feature module 145 extracts between 10 features and 100,00 features. In various embodiments, the lymph node feature module 145 extracts between 100 features and 1000 features. In various embodiments, the lymph node feature module 145 extracts between 300 features and 900 features. In various embodiments, the lymph node feature module 145 extracts between 500 features and 1000 features. In various embodiments, the lymph node feature module 145 extracts between 500 features and 900 features. In various embodiments, the lymph node feature module 145 extracts between 700 features and 1000 features. In various embodiments, the lymph node feature module 145 extracts between 700 features and 900 features. In various embodiments, the lymph node feature module 145 extracts between 800 features and 1000 features. In various embodiments, the lymph node feature module 145 extracts between 800 features and 900 features.

In various embodiments, the lymph node feature module 145 provides the extracted features to the imputation module 150 for training or deploying the imputation model. For example, if the extracted features are derived from training images captured from reference individuals, the lymph node feature module 145 provides the extracted features to the imputation module 150. In various embodiments, the lymph node feature module 145 provides the extracted features to the risk training module 155 for training the risk model. For example, if the extracted features are derived from training images captured from reference individuals, the lymph node feature module 145 provides the extracted features to the risk training module 155 for training the risk model. In various embodiments, the lymph node feature module 145 provides the extracted features to the risk deployment module 160 for deploying the risk model. For example, if the extracted features are derived from images captured from a subject (e.g., subject 110 in FIG. 1A), the lymph node feature module 145 provides the extracted features to the risk deployment module 160.

III.A. Training an Imputation Model

The imputation module 150 trains and deploys an imputation model. Generally, the imputation model is structured such that it analyzes features extracted from an image including one or more lymph nodes and predicts probabilities for the one or more lymph nodes that the lymph nodes are cancerous. Thus, based on the extracted features from an image including one or more lymph nodes, the imputation model imputes a probability for each of the lymph nodes, an imputed probability indicating a likelihood that the lymph node is cancerous (e.g., metastatic cancer). Put another way, the imputation model discriminates between cancerous and non-cancerous lymph nodes by determining risks of metastatic cancer at the lymph-node level.

In various embodiments, the imputation model is any one of a regression model (e.g., linear regression, logistic regression, or polynomial regression), decision tree, random forest, support vector machine, Naïve Bayes model, k-means cluster, or neural network (e.g., feed-forward networks, convolutional neural networks (CNN), deep neural networks (DNN), autoencoder neural networks, generative adversarial networks, or recurrent networks (e.g., long short-term memory networks (LSTM), bi-directional recurrent networks, deep bi-directional recurrent networks), or any combination thereof. In particular embodiments, the imputation model is a random forest classifier or a least absolute shrinkage and selection operator (LASSO) classifier. In various embodiments, the imputation model is a machine learned model. In various embodiments, the imputation model is a boosted gradient machine learning model (e.g., xgboost).

The imputation model can be trained using a machine learning implemented method, such as any one of a linear regression algorithm, logistic regression algorithm, decision tree algorithm, support vector machine classification, Naïve Bayes classification, K-Nearest Neighbor classification, random forest algorithm, deep learning algorithm, gradient boosting algorithm, and dimensionality reduction techniques such as manifold learning, principal component analysis, factor analysis, autoencoder regularization, and independent component analysis, or combinations thereof. In various embodiments, the imputation model is trained using supervised learning algorithms, unsupervised learning algorithms, semi-supervised learning algorithms (e.g., partial supervision), weak supervision, transfer, multi-task learning, or any combination thereof.

In various embodiments, the imputation model has one or more parameters, such as hyperparameters or model parameters. Hyperparameters are generally established prior to training. Examples of hyperparameters include the learning rate, depth or leaves of a decision tree, number of hidden layers in a deep neural network, number of clusters in a k-means cluster, penalty in a regression model, and a regularization parameter associated with a cost function. Model parameters are generally adjusted during training. Examples of model parameters include weights associated with nodes in layers of neural network, support vectors in a support vector machine, and coefficients in a regression model. The model parameters of the imputation model are trained (e.g., adjusted) using the training data to improve the predictive capacity of the imputation model.

The imputation module 150 trains the imputation model using training data. The training data can be stored and/or retrieved from training data store 170. In various embodiments, the training data includes extracted features from training images including one or more lymph nodes obtained from reference individuals. In various embodiments, reference individuals includes healthy individuals (e.g., control individuals). In various embodiments, reference individuals include individuals previously diagnosed with cancer. In various embodiments, reference individuals include individuals previously diagnosed with cancer that has metastasized to the lymph nodes. Therefore, images captured from such individuals include one or more cancerous lymph nodes.

In various embodiments, the training data used for training the imputation model includes reference ground truths that indicate whether a lymph node is cancerous (hereafter also referred to as "positive" or "+") or whether a lymph node is non-cancerous (hereafter also referred to as "negative" or "−"). In various embodiments, the reference ground truths in the training data are binary values, such as "1" or "0." For example, a positive lymph node that is cancerous can be identified in the training data with a value of "1" whereas a negative lymph node that is non-cancerous can be identified in the training data with a value of "0." Altogether, the imputation module 150 trains the imputation model using the training data to minimize a loss function such that the imputation model can better predict an outcome (e.g., a probability of lymph node metastatic cancer for a lymph node) based on the input (e.g., extracted features of the lymph node). In various embodiments, the loss function is constructed for any of a least absolute shrinkage and selection operator (LASSO) regression, Ridge regression, or ElasticNet regression.

In various embodiments, the training data can be obtained and/or derived from a publicly available database. For example, the training data can be obtained and/or derived from the National Lung Screening Trial (NLST) which includes nodal stage (N stage) cancer information for reference individuals. In some embodiments, the training data can be obtained and collected independent of publicly available databases e.g., by capturing images of one or more lymph nodes from a plurality of reference individuals. For example, such training data can be a custom dataset. Training data of a custom dataset can be acquired during patient care and therefore, can have corresponding surgical sampling information of the lymph nodes. The training data can include N stage cancer information for the reference individuals e.g., N stage information previously diagnosed by a clinician based on imaging and/or biopsy results for the reference individuals.

In various embodiments, the reference ground truths that indicate whether a lymph node is cancerous is nodal stage (N stage) information that is derived from clinical stage data. For example, the publicly available NLST dataset includes clinical stage information (e.g., stages 1a, 1b, 2a, 2b, 3a, etc.) for reference individuals but does not include lymph node specific information. In other words, the NLST dataset does not distinguish whether individual lymph nodes are cancerous or non-cancerous. In such embodiments, the reference ground truths that indicate whether a lymph node is cancerous can be back calculated based on the N stage information and other characteristics of the reference individual's cancer (e.g., tumor size, tumor location, tumor shape, and/or tumor density) and/or the lymph node (e.g., lymph node size, lymph node density, and/or lymph node shape). As a first example, a reference individual with a N stage of 0 or 1 has not yet encountered cancer metastasis and therefore, the lymph nodes of this reference individual are assigned a reference ground truth of "negative" or non-cancerous. As another example, a reference individual with a N stage of 2 or 3 has encountered cancer metastasis. Therefore, based on the characteristics of the tumor and/or the lymph node, the lymph node is assigned a reference ground truth of "positive" or "negative."

III.B. Deploying an Imputation Model

The imputation module 150 deploys the trained imputation model to analyze features extracted from an image including one or more lymph nodes and predicts probabilities for the one or more lymph nodes that the lymph nodes are cancerous. In various embodiments, the trained imputation model is deployed against a test dataset. In various embodiments, the test dataset and the training dataset used to train the imputation model may be derived from a common dataset. For example, the common dataset may be split into two subsets for training and testing the imputation model. In some embodiments, the common dataset undergoes a 50:50 training:testing dataset split. In some embodiments, the common dataset undergoes a 60:40 training:testing dataset split. In some embodiments, the common dataset undergoes a 80:20 training:testing dataset split.

The deployment of the trained imputation model yields probabilities (e.g., continuous probabilities between 0 and 1) for lymph nodes, each probability indicating whether the corresponding lymph node is likely to be cancerous. In various embodiments, the imputation module 150 provides one or more of the lymph node metastatic risks for the lymph nodes predicted by the imputation model to be used to train the risk model. In various embodiments, the imputation module 150 provides all of the lymph node metastatic risks for the lymph nodes predicted by the imputation model to be used to train the risk model. In various embodiments, the imputation module 150 performs a selection process to identify a subset of the lymph node metastatic risks for the lymph nodes predicted by the imputation model. Thus, the subset of lymph node metastatic risks is subsequently used to train the risk model.

In some embodiments, the imputation module 150 selects the subset of lymph node metastatic risks by comparing the lymph node metastatic risks to a threshold value. If a lymph node metastatic risk for a lymph node is above a threshold value, the lymph node metastatic risk for the lymph node is selected for inclusion in the subset for training the risk model. If a lymph node metastatic risk for a lymph node is below a threshold value, the lymph node metastatic risk for the lymph node is excluded from the subset and therefore, not used for training the risk model.

In various embodiments, the threshold value is a fixed value. In various embodiments, the threshold value is a 50% risk of metastatic cancer. In various embodiments, the threshold value is 30%, 35%, 40%, 45%, 55%, 60%, 65%, 70%, 75%, 80%, 85%, 90%, 95%, or 99% risk of metastatic cancer. In some embodiments, the threshold value is between 30 and 70%. In some embodiments, the threshold value is between 40 and 60%. In some embodiments, the threshold value is between 45 and 55%. In some embodiments, the threshold value is between 48 and 52%. In some embodiments, the threshold value is between 49 and 51%. In various embodiments, the threshold value is variable. In various embodiments, the threshold value is a median intra-subject probability for having cancer.

The imputation module 150 provides the subset of lymph node metastatic risks to the risk training module 155 for training the risk model.

III.C. Training a Risk Model

The risk training module 155 trains the risk model using training data including at least one or more of the lymph node metastatic risks for the lymph nodes predicted by the imputation model. Here, the one or more lymph node metastatic risks may be the subset of lymph node metastatic risks selected by the imputation module 150, as is described above. The subset of lymph node metastatic risks for training the risk model represents a purified training dataset in comparison to the training dataset that was used to train the imputation model. Specifically, the purified training dataset includes the subset of lymph nodes that are more likely to be cancerous whereas lymph nodes that are less likely to be cancerous (but otherwise may represent false positives or be confounding for training the risk model) are removed from the purified training dataset. Thus, by training the risk model with this purified training dataset, the risk model predicts a greater range of probabilities for all of the lymph nodes in those subjects with metastatic disease. More specifically, the risk model is more likely to assign lymph nodes likely to have cancer with a higher lymph node metastatic risk and lymph nodes unlikely to have cancer with a lower lymph node metastatic risk.

In various embodiments, the risk model analyzes features extracted from an image including one or more lymph nodes and predicts a continuous probability for each of the one or more lymph nodes that the lymph node is cancerous. Thus, based on the extracted features from an image including one or more lymph nodes, the risk model determines a probability for each of the lymph nodes, the determined probability indicating a likelihood that the lymph is cancerous (e.g., metastatic cancer). Here, the risk model determines risks of metastatic cancer at the lymph-node level. In various embodiments, the risk model is similar to the imputation model in that both models analyze features extracted from images and predict risks of metastatic cancer at the lymph-node level. However, the risk model is trained using predictions of the imputation model e.g., one or more lymph-node level risks predicted by the imputation model. Altogether, this enables the risk model to predict LN-level risks of metastatic cancer with a greater range of probabilities than the imputed LN-level risks predicted by the imputation model.

The risk model is trained using training data that includes at least one or more lymph node metastatic risks predicted by the imputation model. Here, the one or more lymph node metastatic risks can serve as reference ground truths for training the risk model. In various embodiments, the training data can additionally include extracted features from training images including one or more lymph nodes obtained from reference individuals. In some embodiments, the training images used to train the risk model can be the same training images previously used to train the imputation model. In some embodiments, the training images used to train the risk model are different from the training images previously used to train the imputation model.

In various embodiments, the training data includes individual training examples, such that the risk model is trained using each training example. For example, each training example can include extracted features of one or more lymph nodes of a particular training image as well as a reference ground truth (e.g., lymph node metastatic risk for the same one or more lymph nodes of the particular training image). Thus, for each training example, the risk model is trained to minimize a loss function (e.g., a loss function for any of a least absolute shrinkage and selection operator (LASSO) regression, Ridge regression, or ElasticNet regression).

In various embodiments, the risk model is any one of a regression model (e.g., linear regression, logistic regression, or polynomial regression), decision tree, random forest, support vector machine, Naïve Bayes model, k-means cluster, or neural network (e.g., feed-forward networks, convolutional neural networks (CNN), deep neural networks (DNN), autoencoder neural networks, generative adversarial networks, or recurrent networks (e.g., long short-term memory networks (LSTM), bi-directional recurrent networks, deep bi-directional recurrent networks), or any combination thereof. In particular embodiments, the risk model is a random forest classifier or a least absolute shrinkage and selection operator (LASSO) classifier. In various embodiments, the risk model is a machine learned model.

The risk model can be trained using a machine learning implemented method, such as any one of a linear regression algorithm, logistic regression algorithm, decision tree algorithm, support vector machine classification, Naïve Bayes classification, K-Nearest Neighbor classification, random forest algorithm, deep learning algorithm, gradient boosting algorithm, and dimensionality reduction techniques such as manifold learning, principal component analysis, factor analysis, autoencoder regularization, and independent component analysis, or combinations thereof. In various embodiments, the risk model is trained using supervised learning algorithms, unsupervised learning algorithms, semi-supervised learning algorithms (e.g., partial supervision), weak supervision, transfer, multi-task learning, or any combination thereof.

In various embodiments, the risk model has one or more parameters, such as hyperparameters or model parameters. Hyperparameters are generally established prior to training. Examples of hyperparameters include the learning rate, depth or leaves of a decision tree, number of hidden layers in a deep neural network, number of clusters in a k-means cluster, penalty in a regression model, and a regularization parameter associated with a cost function. Model parameters are generally adjusted during training. Examples of model parameters include weights associated with nodes in layers of neural network, support vectors in a support vector machine, and coefficients in a regression model. The model parameters of the risk model are trained (e.g., adjusted) using the training data to improve the predictive capacity of the risk model.

III.C. Deploying a Risk Model

The risk deployment module 160 deploys the risk model to determine a subject level risk of metastatic cancer for a subject (e.g., subject 110 described above in FIG. 1A). Here, the risk deployment module 160 provides the extracted features of images including one or more lymph nodes captured from the subject as input to the trained risk model. The trained risk model analyzes the extracted features and outputs probabilities for the lymph nodes that indicate whether individual lymph nodes are likely to be cancerous.

In various embodiments, following deployment of the risk model, the risk deployment module 160 transitions from individual lymph node level risks of metastatic cancer predicted by the risk model to a subject level risk of metastatic cancer for the subject. In various embodiments, the risk deployment module 160 combines the individual lymph node level risks of metastatic cancer to determine the subject level risk of metastatic cancer. In various embodiments, the risk deployment module 160 performs a statistical operation across the lymph node level risks of metastatic cancer. The statistical operation can identify a maximum value, minimum value, average value, median value, or mode value across the individual lymph node level risks of metastatic cancer. In particular embodiments, the statistical operation is a maximum value across the individual lymph node level risks of metastatic cancer. Therefore, the lymph node with the highest lymph node level risk of metastatic disease is assigned as the subject level risk of metastatic disease for the subject.

The cancer staging module 165 determines a cancer stage for the subject based on the subject level risk of metastatic disease for the subject. In various embodiments, the cancer staging module 165 determines a cancer stage for the subject by comparing the subject level risk of metastatic disease for the subject to one or more threshold risk values. These threshold risk values can serve as cutoffs for determining whether a cancer in the subject is likely in any of stage 0, stage 1, stage 2, or stage 3.

In some embodiments, if the subject level risk is greater than 30%, the subject is categorized as having at least stage 3 cancer. In some embodiments, if the subject level risk is greater than 40%, greater than 50%, greater than 60%, greater than 70%, greater than 80%, or greater than 90% risk, the subject is categorized as having at least stage 3 cancer.

In various embodiments, the threshold risk values define risk ranges corresponding to one or more cancer stages. Thus, threshold risk values set the upper and lower bounds of the risk ranges. In some embodiments, if the subject level risk is between 30% and 100%, the subject is categorized as having nodal stage 3 cancer. In some embodiments, if the subject level risk is between 40% and 100%, the subject is categorized as having nodal stage 3 cancer. In some embodiments, if the subject level risk is between 50% and 100%, the subject is categorized as having nodal stage 3 cancer.

In some embodiments, if the subject level risk is between 10% and 40%, the subject is categorized as having nodal stage 2 cancer. In some embodiments, if the subject level risk is between 15% and 40%, the subject is categorized as having nodal stage 2 cancer. In some embodiments, if the subject level risk is between 20% and 40%, the subject is categorized as having nodal stage 2 cancer. In some embodiments, if the subject level risk is between 30% and 40%, the subject is categorized as having nodal stage 2 cancer. In some embodiments, if the subject level risk is between 15% and 30%, the subject is categorized as having nodal stage 2 cancer. In some embodiments, if the subject level risk is between 20% and 30%, the subject is categorized as having nodal stage 2 cancer.

In some embodiments, if the subject level risk is between 5% and 20%, the subject is categorized as having either nodal stage 0 or nodal stage 1 cancer. In some embodiments, if the subject level risk is between 10% and 20%, the subject is categorized as having either nodal stage 0 or nodal stage 1 cancer. In some embodiments, if the subject level risk is between 5% and 15%, the subject is categorized as having either nodal stage 0 or nodal stage 1 cancer. In some embodiments, if the subject level risk is between 8% and 12%, the subject is categorized as having either nodal stage 0 or nodal stage 1 cancer.

IV. Example Method for Cancer Staging

Figure 3A:
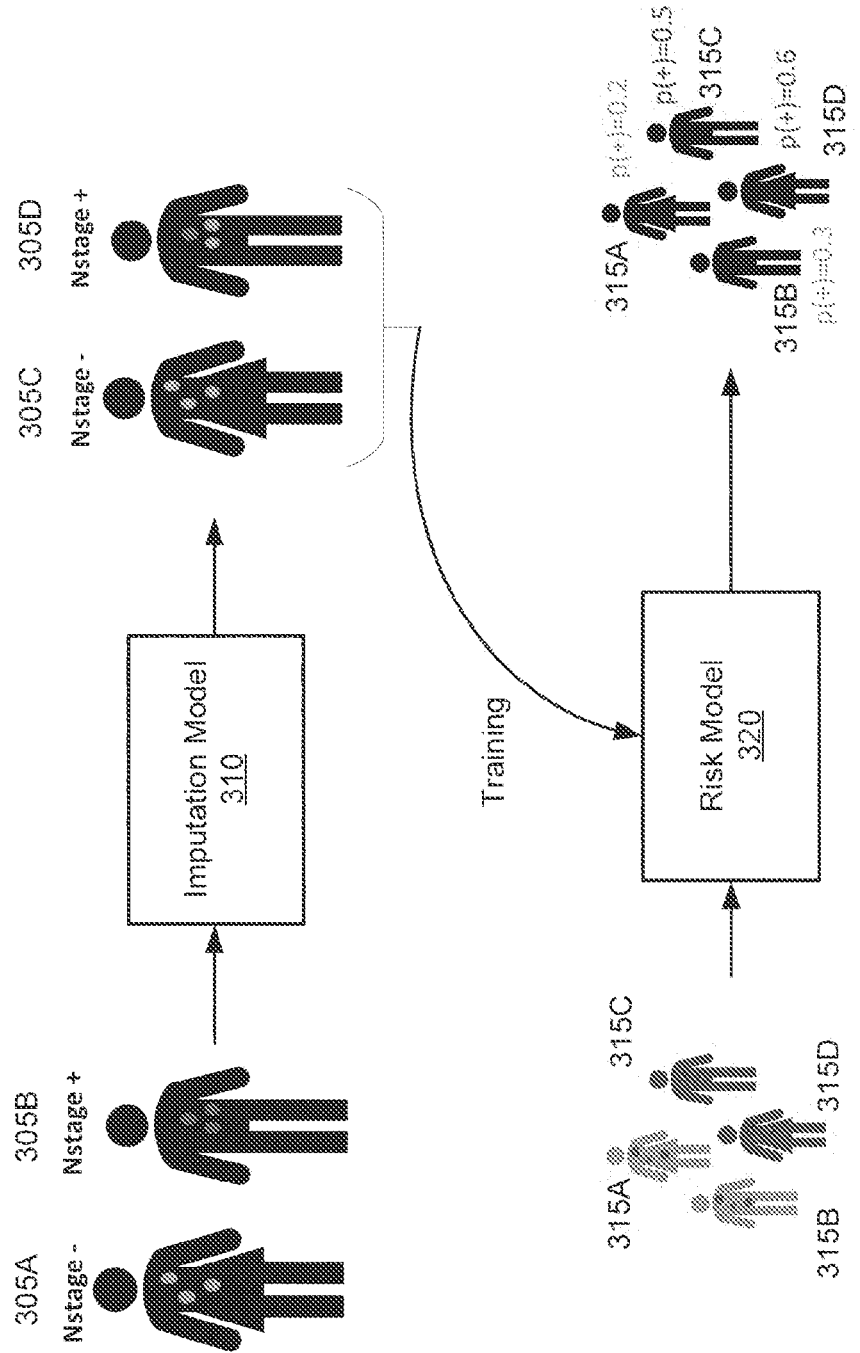
FIG. 3A depicts an example implementation of the imputation model and the risk model, in accordance with an embodiment.

FIG. 3A depicts an example implementation of the imputation model and the risk model, in accordance with an embodiment. Here, reference individuals 305A and 305B may be identified with a particular N stage. For example, reference individual 305A is identified as N stage negative, indicating that reference individual 305A does not exhibit lymph node cancer involvement. Reference individual 305B is identified as N stage positive, indicating that reference individual 305B exhibits lymph node cancer involvement. However, the subject level N stage does not distinguish between particular lymph nodes and whether individual lymph nodes are cancerous or non-cancerous.

The imputation model 310 imputes metastatic risk for each lymph node (e.g., lymph node metastatic risk), thereby enabling the differentiation between lymph nodes with metastatic cancer and lymph nodes that are non-cancerous. In various embodiments, the imputation model 310 predicts a probability for each lymph node that represents a likelihood that the lymph node is cancerous.

As shown in FIG. 3A, the output of the imputation model 310 can identify that individual 305C (corresponding to reference individual 305A) does not exhibit lymph node involvement. In other words, none of the lymph nodes of individual 305C are likely to be cancerous. This confirms the N stage negative identification. Additionally, the output of imputation model 310 can identify that individual 305D (corresponding to reference individual 305B) exhibits lymph node involvement for one or more lymph nodes. For example, the imputation model 310 can impute probabilities such that exactly one lymph node in individual 305D is identified as cancerous whereas other lymph nodes in individual 305D are non-cancerous.

In various embodiments, one or more of the lymph node metastatic risks for the lymph nodes predicted by the imputation model 310 are used to train the risk model 320. In various embodiments, all of the lymph node metastatic risks for the lymph nodes predicted by the imputation model 310 are used to train the risk model 320. In various embodiments, a subset of the lymph node metastatic risk corresponding to a subset of the lymph nodes are used to train the risk model 320, thereby enabling the risk model to predict a greater range of probabilities for all of the lymph nodes in those subjects with metastatic disease.

Once trained, the risk model 320 is deployed to predict subject level risk of metastatic cancer for one or more subjects 315. Thus, the risk model 320 is deployed to transition from lymph node level risks of metastatic disease to a subject level risk of metastatic disease. As shown in FIG. 3A, the risk model 320 is deployed to analyze features extracted from images captured from individuals 315. The risk model 320 predicts subject level risks of metastatic cancer for reach of the individuals 315. For example, the risk model 320 predicts a 20% risk of metastatic cancer for individual 315A, a 30% risk of metastatic cancer for individual 315B, a 50% risk of metastatic cancer for individual 315C, and a 60% risk of metastatic cancer for individual 315D. Thus, individuals 315A and 315B can be categorized with an earlier stage cancer (e.g., stage 0 or 1) whereas individuals 315C and 315D can be categorized with a later stage cancer (e.g., stage 2, 3, or 4).

Individuals 315 can receive different treatments according to their subject level risk of metastatic disease. For example, individuals 315A and 315B who are at low risk of having lymph node metastasis could proceed directly to immediate therapy such as surgical resection or combined bronchoscopic diagnosis and treatment. As another example, individuals 315C and 315D who are at higher risk of having lymph node metastasis can receive additional testing such as PET scanning and lymph node biopsy.

Figure 3B:
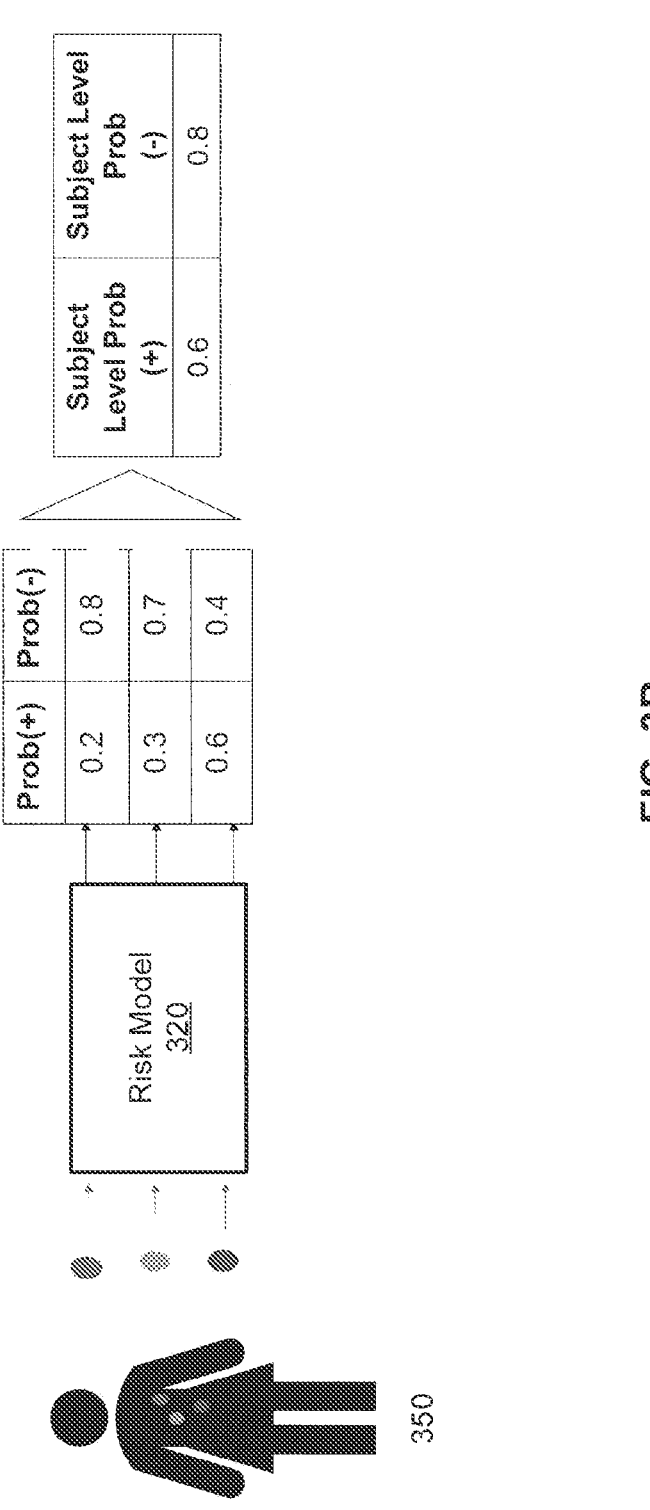
FIG. 3B depicts the implementation of the risk model in further detail, in accordance with an embodiment.

FIG. 3B depicts the implementation of the risk model 320 in further detail, in accordance with an embodiment. Here, the risk model 320 analyzes extracted features from an image captured from subject 350 and outputs probabilities for each of one or more lymph nodes for a subject. As shown in FIG. 3B, the risk model 320 outputs probabilities for three lymph nodes. In other embodiments, the risk model 320 can output additional or fewer lymph node probabilities for the subject 350.

As shown in FIG. 3B, the risk model 320 predicts that a first lymph node has a 20% probability of being cancerous and conversely, a 80% probability of being non-cancerous. Additionally, the risk model 320 predicts that a second lymph node has a 30% probability of being cancerous and conversely, a 70% probability of being non-cancerous. Additionally, the risk model 320 predicts that a third lymph node has a 60% probability of being cancerous and conversely, a 40% probability of being non-cancerous. The individual lymph node probabilities are analyzed to identify a subject level risk of metastatic cancer. In this example, the maximum lymph node probability of metastatic cancer is taken as the subject level probability of metastatic cancer. The third lymph node with a 60% probability of being cancerous is the highest probability amongst the lymph nodes. Thus, the subject level probability of metastatic cancer for the subject 350 is 60%.

V. Cancers

Methods described herein involve cancer staging by determining a subject level risk of cancer of a subject. In various embodiments, the cancer in the subject can include one or more of: lymphoma, B cell lymphoma, T cell lymphoma, mycosis fungoides. Hodgkin's Disease, myeloid leukemia, bladder cancer, brain cancer, nervous system cancer, head and neck cancer, squamous cell carcinoma of head and neck, kidney cancer, lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, gastrointestinal cancer, renal cancer, genitourinary cancer, pulmonary cancer, esophageal carcinoma, stomach cancer, thyroid cancer, head and neck carcinoma, large bowel cancer, hematopoietic cancer, testicular cancer, colon and/or rectal cancer, uterine cancer, or prostatic cancer. In various embodiments, the cancer can be any one of lung bronchioloalveolar carcinoma (BAC), bladder cancer, a female genital tract malignancy (e.g., uterine serous carcinoma, endometrial carcinoma, vulvar squamous cell carcinoma, and uterine sarcoma), an ovarian surface epithelial carcinoma (e.g., clear cell carcinoma of the ovary, epithelial ovarian cancer, fallopian tube cancer, and primary peritoneal cancer), breast carcinoma, non-small cell lung cancer (NSCLC), a male genital tract malignancy (e.g., testicular cancer), retroperitoneal or peritoneal carcinoma, gastroesophageal adenocarcinoma, esophagogastric junction carcinoma, liver hepatocellular carcinoma, esophageal and esophagogastric junction carcinoma, cervical cancer, cholangiocarcinoma, pancreatic adenocarcinoma, extrahepatic bile duct adenocarcinoma, a small intestinal malignancy, gastric adenocarcinoma, cancer of unknown primary (CUP), colorectal adenocarcinoma, esophageal carcinoma, prostatic adenocarcinoma, kidney cancer, head and neck squamous carcinoma, thymic carcinoma, non-melanoma skin cancer, thyroid carcinoma (e.g., papillary carcinoma), a head and neck cancer, anal carcinoma, non-epithelial ovarian cancer (non-EOC), uveal melanoma, malignant pleural mesothelioma, small cell lung cancer (SCLC), a central nervous system cancer, a neuroendocrine tumor, and a soft tissue tumor. In certain embodiments, the cancer is breast cancer, non-small cell lung cancer, bladder cancer, kidney cancer, colon cancer, and melanoma. In some embodiments, the cancer in the subject can be a metastatic cancer, including any one of bladder cancer, breast cancer, colon cancer, kidney cancer, lung cancer, melanoma, ovarian cancer, pancreatic cancer, prostatic cancer, rectal cancer, stomach cancer, thyroid cancer, or uterine cancer. In particular embodiments, the cancer is a him; cancer. In particular embodiments, the cancer is a type of lung cancer, including any one of small cell lung cancer, non-small cell lung cancer, adenocarcinoma, squamous cell cancer, large cell carcinoma, small cell carcinoma, combined small cell carcinoma, lung sarcoma, lung lymphoma, bronchial carcinoids.

VI. Guided Interventions

Embodiments described herein involve the determination of a cancer staging by determining a subject level risk of metastatic cancer in a subject. In various embodiments, an intervention is provided to a subject based on the cancer staging and/or the subject level risk of metastatic cancer predicted for the subject. Such interventions, hereafter referred to as guided interventions, can be any one of: application of a diagnostic, application of a therapeutic agent, subsequent testing of the subject, subsequent biopsy (e.g., cancer biopsy or lymph node biopsy, bronchoscopic sampling of lymph nodes), subsequent image scanning (e.g., PET scanning, MRI scanning, ultrasound imaging, or X-ray imaging), tumor resection, bronchoscopic diagnosis, selection and/or administration of therapeutic(s), selection/administration of pharmaceutical composition, enrollment in a clinical trial, non-enrollment in a clinical trial, or any combination thereof.

In various embodiments, the subject level risk of metastatic cancer predicted for the subject or the predicted cancer stage indicates that the subject is at high risk of metastatic cancer. In various embodiments, a subject at high risk of metastatic cancer has a predicted subject level risk of metastatic cancer that is above a threshold score. In various embodiments, the threshold score is above 20% risk of metastatic cancer. In various embodiments, the threshold score is above 25% risk of metastatic cancer. In various embodiments, the threshold score is above 30%, above 35%, above 40%, above 45%, above 50%, above 55%, above 60%, above 65%, above 70%, above 75%, above 80%, above 85%, above 9%, above 95%, or above 99% risk of metastatic cancer. In various embodiments, the threshold score is between 20% and 80%. In some embodiments, the threshold value is between 30 and 70%. In some embodiments, the threshold value is between 40 and 60%. In some embodiments, the threshold value is between 45 and 55%. In some embodiments, the threshold value is between 20 and 60%. In some embodiments, the threshold value is between 30 and 55%. In some embodiments, the threshold value is between 35 and 50%. In some embodiments, the threshold value is between 40 and 45%.

In various embodiments, a subject is at high risk of metastatic cancer if the predicted cancer stage for the subject is at least stage 2 (e.g., stage 2 or stage 3). In such embodiments, the guided intervention involves one of subsequent testing of the subject, subsequent biopsy of the subject, or subsequent image scanning of the subject. This allows clinical providers to prioritize the subsequent testing, biopsy, or image scanning of subjects that are at highest risk.

In various embodiments, if the subject is predicted to be at a high risk of metastatic cancer, procedures that are inappropriate for late-stage metastatic cancer can be ruled out for the subject. Examples of such procedures that are ruled out include tumor resection, lung resection, radiation (e.g., external beam radiation), chemotherapy (e.g., local or systemic chemotherapy), immunomodulatory therapy, or even general anesthesia.

In particular embodiments, if the subject is predicted to be at a high risk of metastatic cancer, the subject undergoes a subsequent image scanning to confirm the prediction. For example, if the subject is predicted to be at a high risk of metastatic cancer, the subject further undergoes PET scanning. In such embodiments, if the PET scanning returns a negative result (e.g., no lymph node involvement), the subject can undergo further testing. For example, the subject can further undergo a subsequent biopsy to definitively sample the lymph node. In some embodiments, the subsequent biopsy is a bronchoscopic sampling of lymph nodes.

In particular embodiments, if the subject is predicted to be at a high risk of metastatic cancer, the subject directly undergoes a subsequent biopsy to confirm the prediction. For example, the subject need not undergo subsequent image scanning to confirm the prediction and instead, directly undergoes a subsequent biopsy. For example, if the subject is predicted to be at a high risk of metastatic cancer, the subject further undergoes bronchoscopic sampling of lymph nodes.

As described herein, the subject level risk of metastatic cancer can be determined from individual lymph node level risks across the lymph nodes. Thus, for a subject who is predicted to have high risk of metastatic cancer based on the subject level of risk, the particular lymph node(s) that led to the high subject level of risk can be identified. Thus, those particular lymph nodes can be targeted for subsequent testing or treatment. In particular embodiments, those particular lymph nodes can undergo subsequent image scanning (e.g., PET scanning) to confirm the prediction. In particular embodiments, those particular lymph nodes can undergo a subsequent biopsy to definitively sample the particular lymph nodes. Thus, the subsequent biopsy can confirm the presence or absence of metastatic cancer in those particular lymph nodes.

In various embodiments, if the subject is predicted to be at a high risk of metastatic cancer, the subject can be enrolled in a clinical trial. For example, such a clinical trial may be testing therapeutic efficacy of a treatment against metastatic cancer and therefore, it may specify in its eligibility criteria that enrollees are to be exhibiting metastatic cancer. In various embodiments, if the subject is predicted to be at a high risk of metastatic cancer, the subject is withheld from enrollment in a clinical trial. For example, such a clinical trial may be testing therapeutic efficacy of a treatment against a non-metastatic form of cancer.

In various embodiments, the subject level risk of metastatic cancer predicted for the subject indicates that the subject is at low risk of metastatic cancer. In various embodiments, a subject at low risk of metastatic cancer has a predicted subject level risk that is below a threshold score. In various embodiments, the threshold score is below 20% risk of metastatic cancer. In various embodiments, the threshold score is below 25% risk of metastatic cancer. In various embodiments, the threshold score is below 30%, below 35%, below 40%, below 45%, below 50%, below 55%, below 60%, below 65%, below 70%, below 75%, below 80%, below 85%, below 90%, below 95%, or below 99% risk of metastatic cancer. In some embodiments, the threshold value is between 5% and 40%. In some embodiments, the threshold value is between 10 and 30%. In some embodiments, the threshold value is between 15 and 25%. In some embodiments, the threshold value is between 18 and 22%. In various embodiments, a subject is at low risk of metastatic cancer if the predicted cancer stage for the subject is below stage 2 (e.g., stage 0 or stage 1). In such embodiments, the guided intervention involves one of tumor resection, bronchoscopic diagnosis, selection and/or administration of therapeutic(s), and/or selection/administration of pharmaceutical composition. This enables the rapid identification and treatment of subjects where metastasis has not yet occurred.

In various embodiments, a therapeutic agent can be selected and/or administered to the subject based on the subject level risk of metastatic cancer, the selected therapeutic agent likely to exhibit efficacy against the cancer. Exemplary therapeutic agents include chemotherapies, radiation, antigen-specific monoclonal antibodies, or immunotherapies. In various embodiments, a subject at high risk of metastatic cancer is provided a therapeutic agent. In various embodiments, a subject at high risk of metastatic cancer has a predicted subject level risk of metastatic cancer that is above a threshold score. In various embodiments, the threshold score is above 20% risk of metastatic cancer. In various embodiments, the threshold score is above 25% risk of metastatic cancer. In various embodiments, the threshold score is above 30%, above 35%, above 40%, above 45%, above 50%, above 55%, above 60%, above 65%, above 70%, above 75%, above 80%, above 85%, above 90%, above 95%, or above 99% risk of metastatic cancer. In various embodiments, a subject is at high risk of metastatic cancer if the predicted cancer stage for the subject is at least stage 2 (e.g., stage 2, stage 3, or stage 4).

In various embodiments, a subject at low risk of metastatic cancer is provided a therapeutic agent. In various embodiments, a subject at low risk of metastatic cancer has a predicted subject level risk that is below a threshold score. In various embodiments, the threshold score is below 20% risk of metastatic cancer. In various embodiments, the threshold score is below 25% risk of metastatic cancer. In various embodiments, the threshold score is below 30%, below 35%, below 40%, below 45%, below 50%, below 55%, below 60%, below 65%, below 70%, below 75%, below 80%, below 85%, below 90%, below 95%, or below 99% risk of metastatic cancer. In various embodiments, a subject is at low risk of metastatic cancer if the predicted cancer stage for the subject is below stage 2 (e.g., stage 0 or stage 1).

In various embodiments, if the subject is predicted to be at a low risk of metastatic cancer, the subject can be directed to early-stage cancer treatments. Examples of early-stage cancer treatments include tumor resection, lung resection, chemotherapy (e.g., local or systemic chemotherapy), locally delivered therapies (e.g., transbronchial needle instillation or catheter based ablation), or radiation.

In particular embodiments, if the subject is predicted to be at a low risk of metastatic cancer, the subject undergoes a subsequent image scanning to confirm the prediction. For example, if the subject is predicted to be at a low risk of metastatic cancer, the subject further undergoes PET scanning. In such embodiments, if the PET scanning returns a negative result (e.g., no lymph node involvement), then the PET scan results align with the prediction. However, if the PET scanning returns a positive result (e.g., lymph node involvement), the subject can undergo further testing. For example, the subject can further undergo a subsequent biopsy to definitively sample the lymph node. In some embodiments, the subsequent biopsy is a bronchoscopic sampling of lymph nodes.

In various embodiments the therapeutic agent is a biologic, e.g. a cytokine, antibody, soluble cytokine receptor, anti-sense oligonucleotide, siRNA, etc. Such biologic agents encompass muteins and derivatives of the biological agent, which derivatives can include, for example, fusion proteins, PEGylated derivatives, cholesterol conjugated derivatives, and the like as known in the art. Also included are antagonists of cytokines and cytokine receptors, e.g. traps and monoclonal antagonists. Also included are biosimilar or bioequivalent drugs to the active agents set forth herein.

Therapeutic agents for lung cancer can include chemotherapeutics such as docetaxel, cisplatin, carboplatin, gemcitabine, Nab-paclitaxel, paclitaxel, pemetrexed, gefitinib, erlotinib, brigatinib (Alunbrig®), capmatinib (Tabrecta®), selpercatinib (Retevmo®), entrectinib (Rozlytrek®), lorlatinib (Lorbrena®), larotrectinib (Vitrakvi®), dacomitinib (Vizimpro®), and vinorelbine. Therapeutic agents for lung cancer can include antibody therapies such as durvalumab (Imfinzi®), nivolumab (Opdivo®), pembrolizumab (Keytruda®), atezolizumab (Tecentriq®), and ramucirumab.

In various embodiments, a pharmaceutical composition can be selected and/or administered to the subject based on the subject level risk of metastatic cancer, the selected therapeutic agent likely to exhibit efficacy against the cancer. A pharmaceutical composition administered to an individual includes an active agent such as the therapeutic agent described above. The active ingredient is present in a therapeutically effective amount, i.e., an amount sufficient when administered to treat a disease or medical condition mediated thereby. The compositions can also include various other agents to enhance delivery and efficacy, e.g. to enhance delivery and stability of the active ingredients. Thus, for example, the compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents. The composition can also include any of a variety of stabilizing agents, such as an antioxidant.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, or intracranial method. In various embodiments, pharmaceutical compositions can be administered via catheter based deployment (e.g., using flexible or rigid robotic based bronchoscopy).

Such a pharmaceutical composition may be administered for treatment (e.g., after diagnosis of a patient with lung cancer) purposes. Preventing, prophylaxis or prevention of a disease or disorder as used in the context of this invention refers to the administration of a composition to prevent the occurrence, onset, progression, or recurrence of lung cancer some or all of the symptoms of lung cancer or to lessen the likelihood of the onset of lung cancer. Treating, treatment, or therapy of lung cancer shall mean slowing, stopping or reversing the cancer's progression by administration of treatment according to the present invention. In the preferred embodiment, treating lung cancer means reversing the cancer's progression, ideally to the point of eliminating the cancer itself.

VII. Computer Implementation

The methods of the invention, including the methods of for cancer staging by determining a subject level risk of metastatic cancer of a subject, are, in some embodiments, performed on one or more computers.

For example, the building and deployment of an imputation model and/or risk model and database storage can be implemented in hardware or software, or a combination of both. In one embodiment of the invention, a machine-readable storage medium is provided, the medium comprising a data storage material encoded with machine readable data which, when using a machine programmed with instructions for using said data, is capable of displaying any of the datasets and execution and results of the models described herein. The invention can be implemented in computer programs executing on programmable computers, comprising a processor, a data storage system (including volatile and non-volatile memory and/or storage elements), a graphics adapter, a pointing device, a network adapter, at least one input device, and at least one output device. A display is coupled to the graphics adapter. Program code is applied to input data to perform the functions described above and generate output information. The output information is applied to one or more output devices, in known fashion. The computer can be, for example, a personal computer, microcomputer, or workstation of conventional design.

Each program can be implemented in a high-level procedural or object-oriented programming language to communicate with a computer system. However, the programs can be implemented in assembly or machine language, if desired. In any case, the language can be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system can also be considered to be implemented as a computer-readable storage medium, configured with a computer program, where the storage medium so configured causes a computer to operate in a specific and predefined manner to perform the functions described herein.

The signature patterns and databases thereof can be provided in a variety of media to facilitate their use. "Media" refers to a manufacture that contains the signature pattern information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure can be chosen, based on the means used to access the stored information. A variety of data processor programs and formats can be used for storage, e.g. word processing text file, database format, etc.

In some embodiments, the methods of the invention, including the methods for cancer staging by determining a subject level risk of metastatic cancer of a subject, are performed on one or more computers in a distributed computing system environment (e.g., in a cloud computing environment). In this description, "cloud computing" is defined as a model for enabling on-demand network access to a shared set of configurable computing resources. Cloud computing can be employed to offer on-demand access to the shared set of configurable computing resources. The shared set of configurable computing resources can be rapidly provisioned via virtualization and released with low management effort or service provider interaction, and then scaled accordingly. A cloud-computing model can be composed of various characteristics such as, for example, on-demand self-service, broad network access, resource pooling, rapid elasticity, measured service, and so forth. A cloud-computing model can also expose various service models, such as, for example, Software as a Service ("SaaS"), Platform as a Service ("PaaS"), and Infrastructure as a Service ("IaaS"). A cloud-computing model can also be deployed using different deployment models such as private cloud, community cloud, public cloud, hybrid cloud, and so forth. In this description and in the claims, a "cloud-computing environment" is an environment in which cloud computing is employed.

Figure 4:
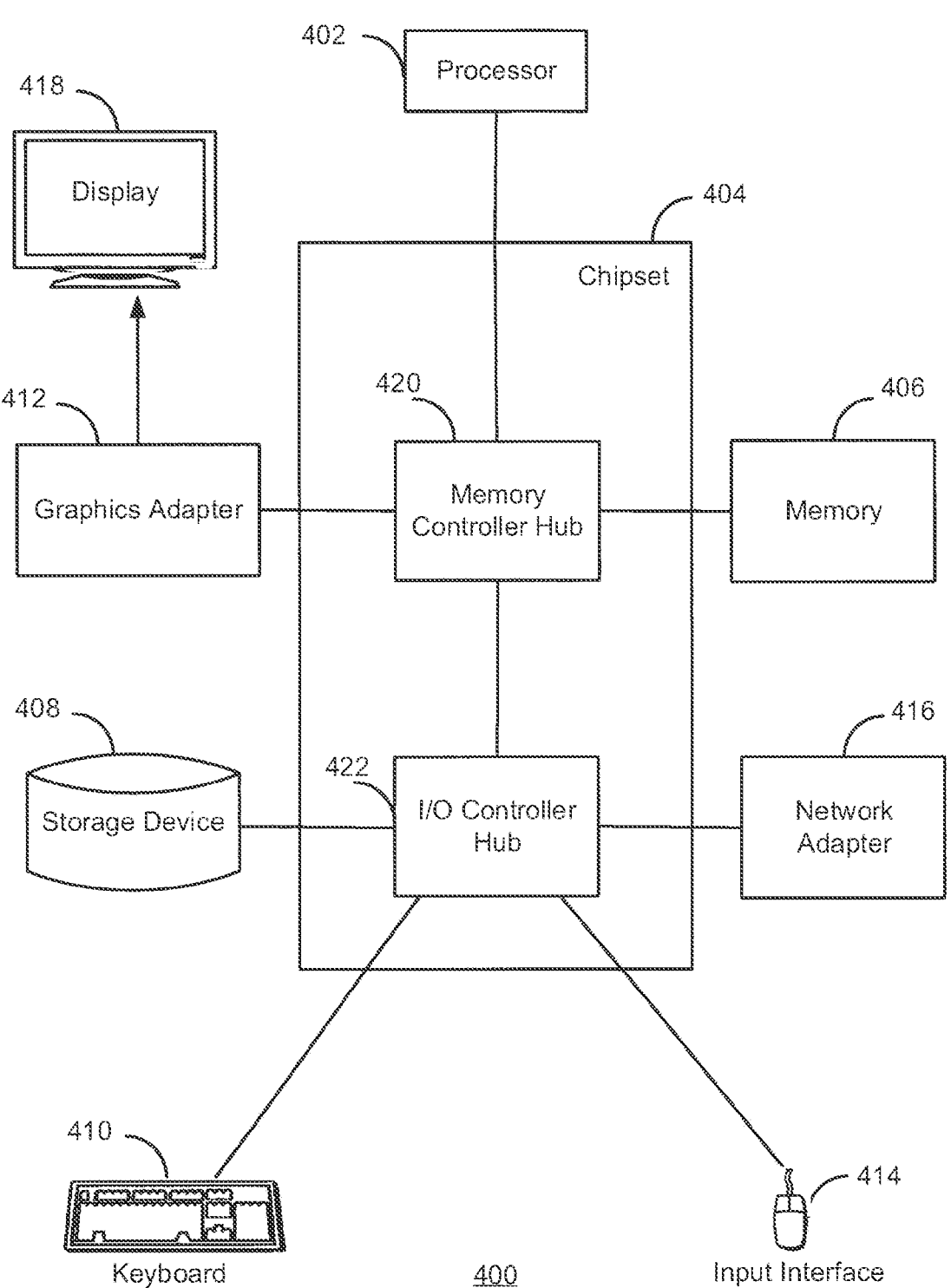
FIG. 4 illustrates an example computer for implementing the entities shown in FIGS. 1A, 1B, 2A, 2B, 3A, and 3B.

FIG. 4 illustrates an example computer for implementing the entities shown in FIGS. 1A, 1B, 2A, 2B, 3A, and 3B. The computer 400 includes at least one processor 402 coupled to a chipset 404. The chipset 404 includes a memory controller hub 420 and an input/output (I/O) controller hub 422. A memory 406 and a graphics adapter 412 are coupled to the memory controller hub 420, and a display 418 is coupled to the graphics adapter 412. A storage device 408, an input device 414, and network adapter 416 are coupled to the I/O controller hub 422. Other embodiments of the computer 400 have different architectures.

The storage device 408 is a non-transitory computer-readable storage medium such as a hard drive, compact disk read-only memory (CD-ROM), DVD, or a solid-state memory device. The memory 406 holds instructions and data used by the processor 402. The input interface 414 is a touch-screen interface, a mouse, track ball, or other type of pointing device, a keyboard, or some combination thereof, and is used to input data into the computer 400. In some embodiments, the computer 400 may be configured to receive input (e.g., commands) from the input interface 414 via gestures from the user. The graphics adapter 412 displays images and other information on the display 418. The network adapter 416 couples the computer 400 to one or more computer networks.

The computer 400 is adapted to execute computer program modules for providing functionality described herein. As used herein, the term "module" refers to computer program logic used to provide the specified functionality. Thus, a module can be implemented in hardware, firmware, and/or software. In one embodiment, program modules are stored on the storage device 408, loaded into the memory 406, and executed by the processor 402.

The types of computers 400 used by the entities of FIG. 1A or 1B can vary depending upon the embodiment and the processing power required by the entity. For example, the cancer staging system 130 can run in a single computer 400 or multiple computers 400 communicating with each other through a network such as in a server farm. The computers 400 can lack some of the components described above, such as graphics adapters 412, and displays 418.

VIII. Systems

Further disclosed herein are systems for cancer staging by determining a subject level risk of metastatic cancer of a subject. In various embodiments, such a system can include at least the cancer staging system 130 described above in FIG. 1A. In various embodiments, the cancer staging system 130 is embodied as a computer system, such as a computer system with example computer 400 described in FIG. 4.

In various embodiments, the system includes an imaging device, such as imaging device 120 described above in FIG. 1A. In various embodiments, the system includes both the cancer staging system 130 (e.g., a computer system) and an imaging device. In such embodiments, the cancer staging system 130 can be communicatively coupled with the imaging device 120 to receive images (e.g., CT scans) captured from a subject. The computer system implements, in silico, one or both of the imputation model and the risk model to analyze the images and to determine a subject level risk of nodal disease for the subject.

EXAMPLES

Below are examples of specific embodiments for carrying out the present invention. The examples are offered for illustrative purposes only and are not intended to limit the scope of the present invention in any way. Efforts have been made to ensure accuracy with respect to numbers used (e.g., amounts, temperatures, etc.), but some experimental error and deviation should be allowed for.

Example 1: Study Population and Feature Extraction

This study was performed using data from the CT arm of the National Lung Screening Trial (NLST). This sub-cohort of NLST included data from 658 study participants, 301 with benign nodules and 357 with lung cancer. Each CT scan of the 658 study participants was inspected and up to 21 lymph node stations (16+/−6 per person) were annotated (9,969 LN annotated; 4,631 LN in controls and 5,318 LN in those with lung cancer). From this initial sample, 288 people with lung cancer had staging data available for analyses. To create a balanced initial cohort, 287 control subjects were identified. The lymph node stations are depicted in FIG. 2A and detailed in Table 1.

27

TABLE 1

Lymph node annotations by station

| | #LN (per subject average) | |
| Lymph Station | Control Group | Cancer Group |
|---|---|---|
| 1L | 34 | 22 |
| 1R | 29 | 13 |
| 2L | 191 | 186 |
| 2R | 732 | 879 |
| 3A | 203 | 263 |
| 3P | 133 | 139 |
| 4L | 430 | 459 |
| 4R | 837 | 987 |
| 5 | 386 | 457 |
| 6 | 189 | 132 |
| 7 | 477 | 541 |
| 8L | 212 | 230 |
| 8R | 140 | 215 |
| 9L | 29 | 98 |
| 9R | 8 | 14 |
| 10L | 181 | 188 |
| 10R | 92 | 60 |
| 11L | 74 | 106 |
| 11R | 57 | 59 |
| 12L | 5 | 4 |
| 12R | 5 | 8 |

For each LN station, a spherical region with 5 mm and 7.5 mm radii was defined. The sphere center defined by the annotation label. An example of two LN annotations is shown in FIG. 2B.

These smaller (5 mm) and larger (7.5 mm) spherical ROIs (regions of interest) were used to explore the extent of the image to be used for model building From these spherical ROIs, 3 separate radiomics panels were extracted with 6 feature categories each. Each panel varied in the number of metrics they utilized, and it was based on a different transformation of the CT. Panel 1 used the original image as input for the feature extraction. Panel 2 and 3 employed the Wavelet transform and the Laplacian of Gaussians (LoG) transformation of the input image respectively. Feature categories included first order features, shape features, gray level co-occurrence matrix 1 (GLCM) features, gray level run length matrix (GLRLM) features, gray level size zone matrix (GLSZM) features, and neighborhood gray tone difference matrix (NGTDM) features). The breakdown of features is shown in Table 3.

TABLE 3

Features from CT scan images.
Number of Features
Feature Category

| Image Cat | First Order | Shape* | GLCM | GLRLM | GLSZM | NGTDM |
|---|---|---|---|---|---|---|
| Original | 22 | 14 | 24 | 16 | 16 | 5 |
| Wavelet | 144 | 0 | 192 | 128 | 128 | 40 |
| LoG | 18 | 0 | 24 | 16 | 16 | 5 |

Figure 5A:
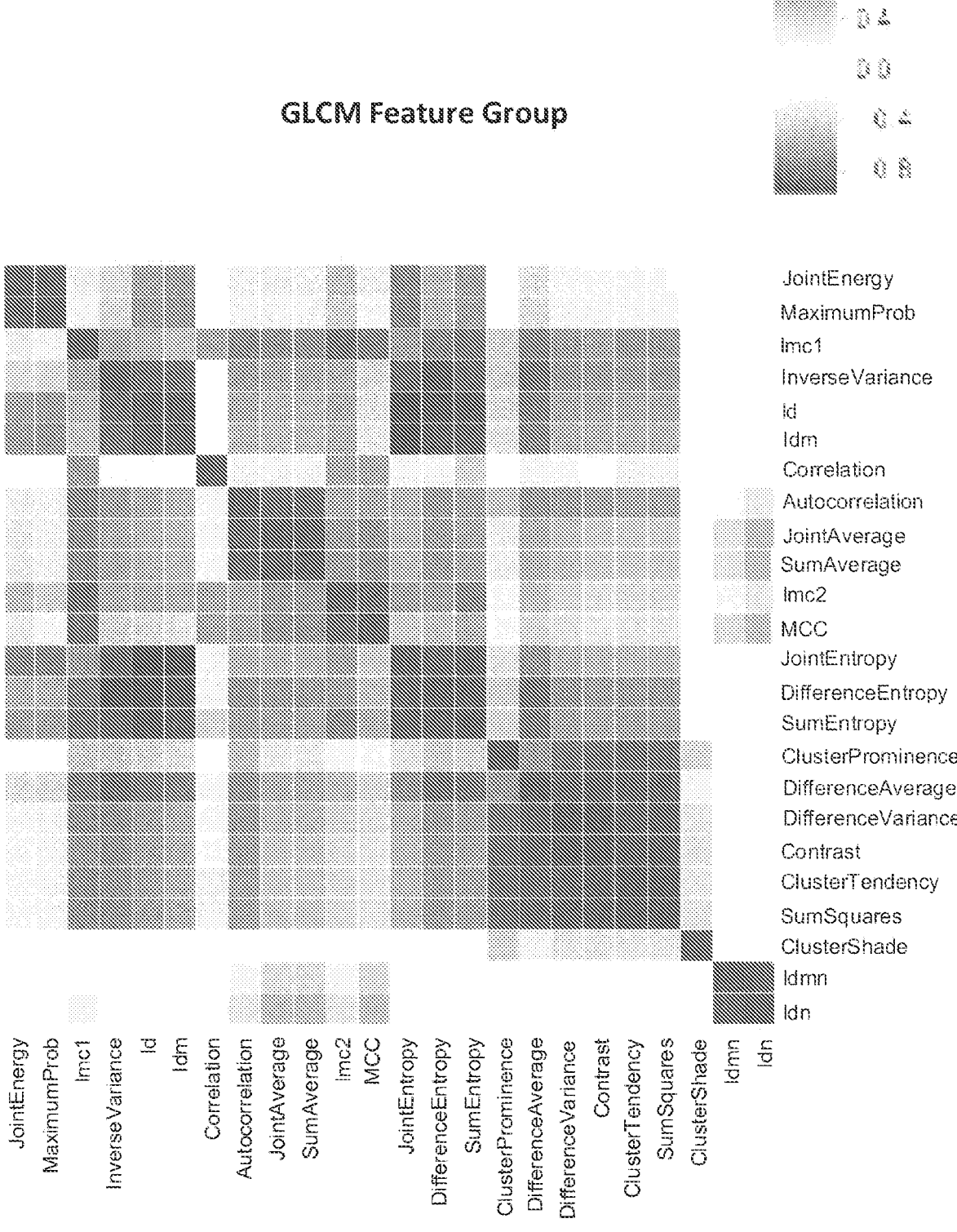
FIGS. 5A-5R depict example correlation heat maps of different lymph node radiomic features.
Figure 5B:
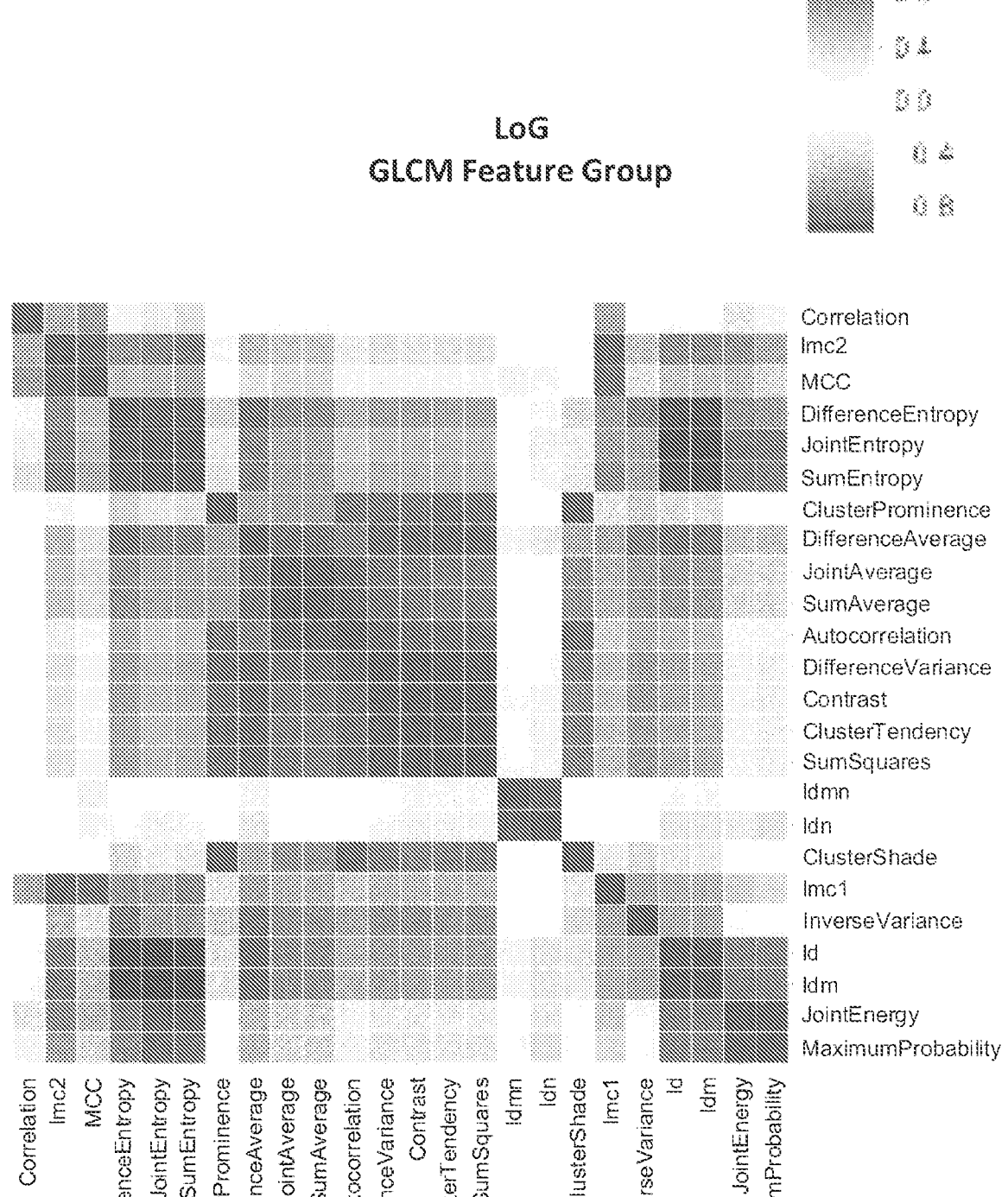
Figure 5I:
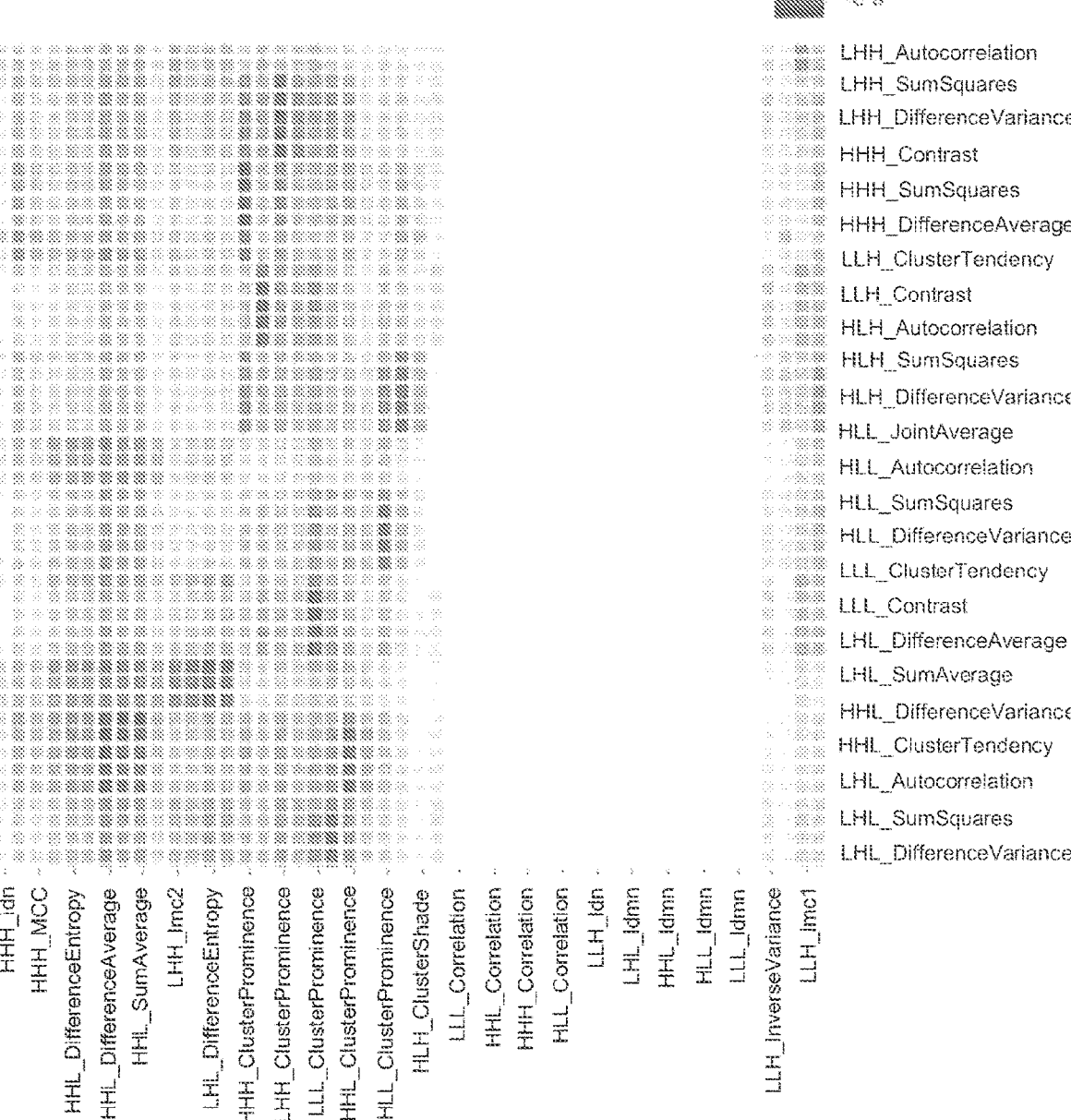

*Shape features where not included in the LN analysis as each station was analyzed with fixed spherical shapes regions FIGS. 5A-5R depict example correlation heat maps of different lymph node radiomic features across the different panels for the GLCM feature category. Additionally, FIGS. 5A-5R each show specific features. Examples of such features shown in FIGS. 5A-5R include correlation features, LMC2, MCC, Difference in Entropy, Joint Entropy, Sum of Entropy, Cluster prominence, average difference, joint average, sum of average, autocorrelation, difference in variance, contrast, cluster tendency, sum of squares, LDMN, LDN, Cluster shade, LMC1, Inverse variance, LD, LDM, joint energy, and maximum probability. FIGS. 5C-5R show the features with respect to different filters. Specifically, FIGS. 5C-5R provide designations of "XYZ" where "X", "Y", and "Z" each refer to a filter applied to the X, Y, or Z directions of the image. A "H" refers to a high pass filter whereas a "L" refers to a low pass filter. Therefore, a designation of "HHH" refers to features derived from a 3D image that has undergone high pass filtering in each of the X, Y, and Z directions. A designation of "HHL" refers to features derived from a 3D image that has undergone high pass filtering in the X and Y directions, and has undergone low pass filtering in the Z direction.

Example 2: Imputation Model for Cancer Staging

The modeling began with the prediction of cancer involvement for each lymph node. To do this, the cancer stage (reported in NLST) was imputed to each annotated LN station (individual LN data was not reported in the NLST so LN involvement was "backed out" from the cancer stage). The data were then split 50:50 for Training:Testing with the distribution of those data provided in Table 2.

TABLE 2

Example 50:50 splitting of data

| | Training | | Testing | |
| N stage | Control | Cancer | Control | Cancer |
|---|---|---|---|---|
| 0 | 2337 | 2179 | 2263 | 1713 |
| 1 | 0 | 127 | 0 | 73 |
| 2 | 0 | 125 | 0 | 342 |
| 3 | 0 | 40 | 0 | 42 |

Figure 6:
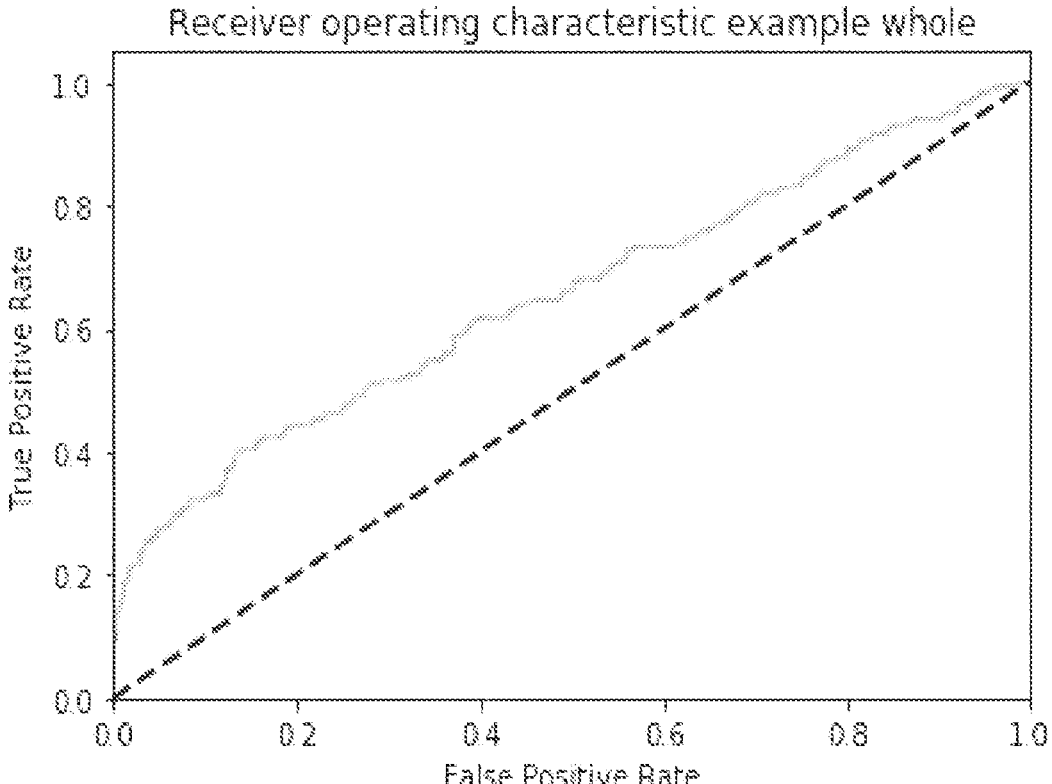
FIG. 6 depicts lymph node level performance of an imputation model.

The outcome of the model was binary (Nodal metastases yes/no using the Nstage covariable in the NLST data set. "No" was N=0 or N=1 and "yes" was N=2 or N=3). The metrics were normalized (z-score) and Random Forest and LASSO Classifiers were trained and tested. For each LN, a continuous probability that it was cancerous was generated. For example, there could be a LN with a 20% probability of being cancerous (by subtraction means it was assigned an 80% probability of being free of cancer). All LN within and across study participants were considered to be independent data. The performance of the initial model is shown in FIG. 6. Specifically, the model achieved an Area under the Curve (AUC)=65.3%, Accuracy (ACC)=96.6%, Sensitivity=61.2%, and Specificity=60.8%.

The limitation to the NLST data is that LN specific information was not available and on average 16 LN were annotated and underwent radiomics based assessment in each person. This model therefore assumed that all LN within a patient with metastatic cancer were "+" when in clinical medicine, there is typically only 1 LN that has cancerous cells (cancer doesn't spread to all LN simultaneously but generally to only one or two LN). Therefore, imputing individual LN involvement from subject level cancer stage introduces false positives that confounds model performance at the LN level (again, because all LN within that person's CT scan are assumed to be "+").

Figure 7A:
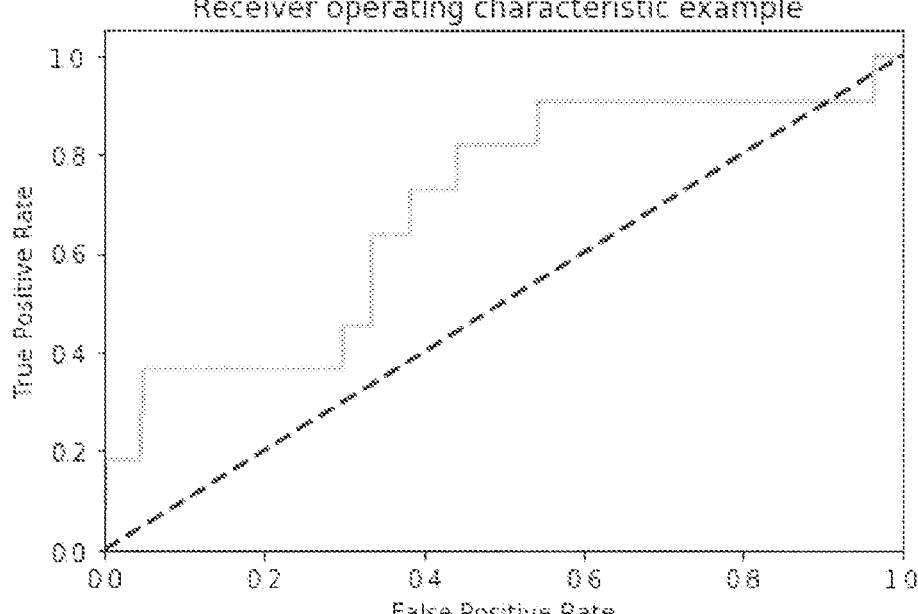
FIGS. 7A and 7B depict subject level performance using the highest probability score predicted by the LN-level classifier.
Figure 7B:
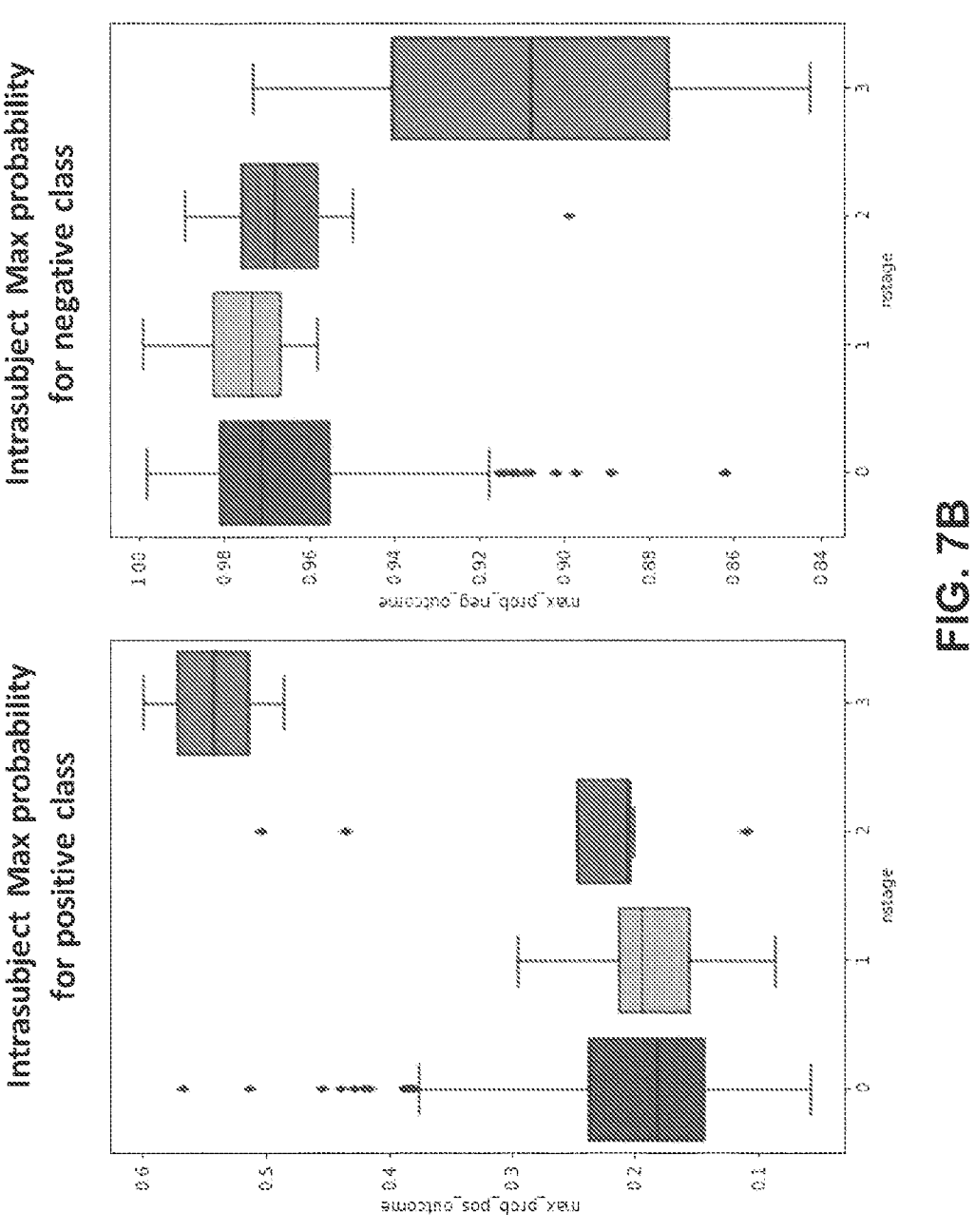
Figure 8:
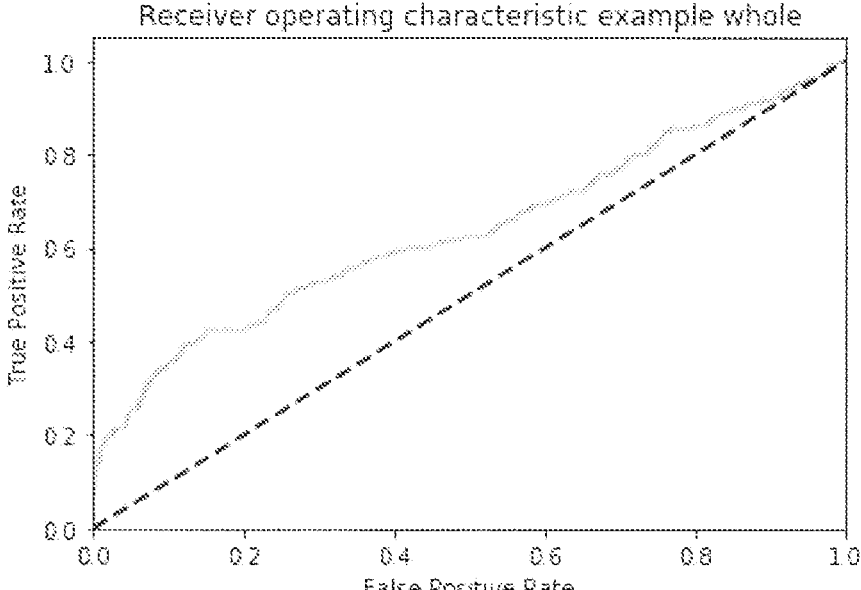
FIG. 8 depicts lymph node level performance an imputation model in the two step bootstrap approach.

The N stage likelihood was then determined using the highest probability score predicted by the LN-level classifier for all the LN stations of a given subject. FIGS. 7A-7B depict the subject level performance (AUC=69.1%, Sensitivity=72.7%, and Specificity=61.6%) based on the N stage likelihoods. The distribution of scores (e.g., max probabilities) were also plotted across N stages as shown in FIG. 7B. Here, a higher max probability was observed for cases with stage 3 cancer (left panel).

Example 3: Step-up Lymph Node Classification Approach: Bootstrapping Intra-Patient LNs A two-step bootstrap approach was performed to transition from LN level risk of metastatic disease to subject level risk of metastatic disease. In particular, the two-step bootstrap approach included the implementation of an imputation model and a risk model, as described above in reference to FIG. 3A. Here, the challenge was that a subject's N stage is imputed to all the LN stations to train a classifier. This imputation introduces error at the LN station given that most LN are cancer free.

The two steps were as follows:
1. IMPUTATION: The lymph nodes most likely to be involved by cancer was identified for each subject with known metastatic disease. This was done for each subject by selecting the LNs with probabilities of being cancerous (output from last model) above the median intrasubject value (Imputation process involving the imputation model shown in FIG. 3A). LN below the median intra-subject probability for having cancer were classified as negative.
2. CLASSIFICATION: The cohort was split 50:50 training:testing. A second classifier (e.g., risk model 320 in FIG. 3A) was then trained using the imputed pool of LN outcomes to predict the presence nodal disease for each subject.

The output of this model was continuous probability of each LN being cancerous similar to the output of the model described above in Example 2. However, the benefit of the additional Imputation and Classification steps was that there was now a greater range of probabilities assigned for all of the lymph nodes in those subjects with metastatic disease. More specifically, those LN likely to have cancer had a higher probability of being "+" while those unlikely to have cancer had a lower probability of being "+". For the prediction step, a subject-level score of LN involvement was generated based on the LN with the highest probability (FIG. 3B). Specifically, this involved taking LN specific probabilities and providing a subject specific probability of having LN involvement of their lung cancer. In the test subject shown in FIG. 3B, the bottom LN was assigned a 60% chance of harboring cancer (e.g., Prob (+)=0.6). This was the LN with the highest "+" probability from amongst the three LN. Thus, the subject level probability was assigned the value of 0.6.

Figure 9A:
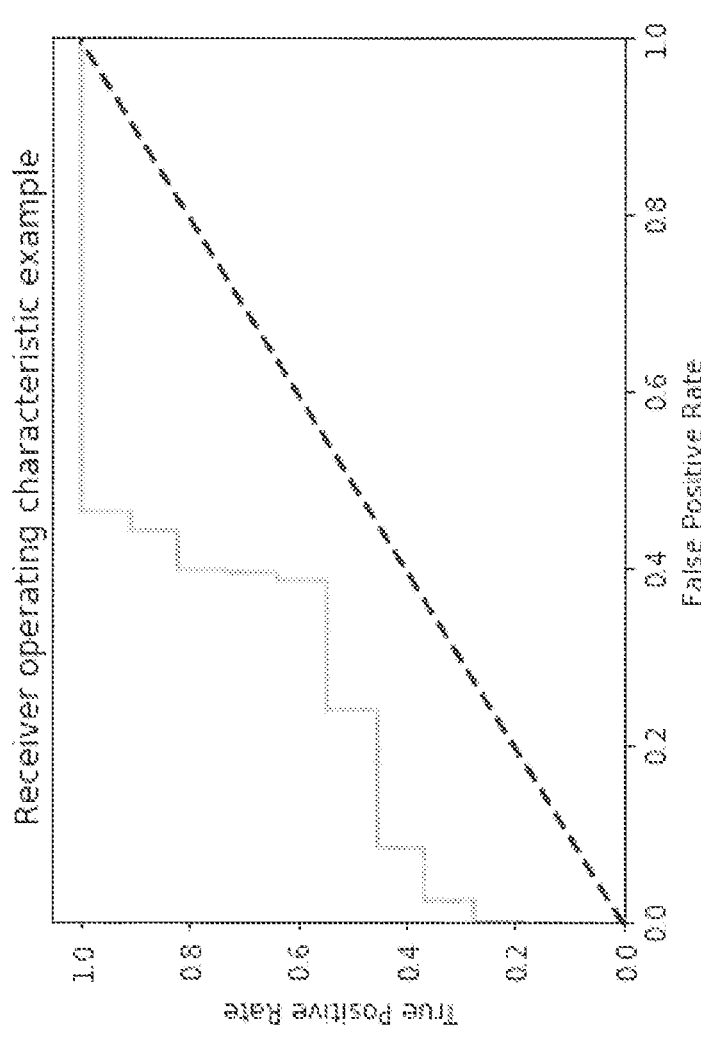
FIGS. 9A and 9B depict subject level performance using the bootstrap approach.
Figure 9B:
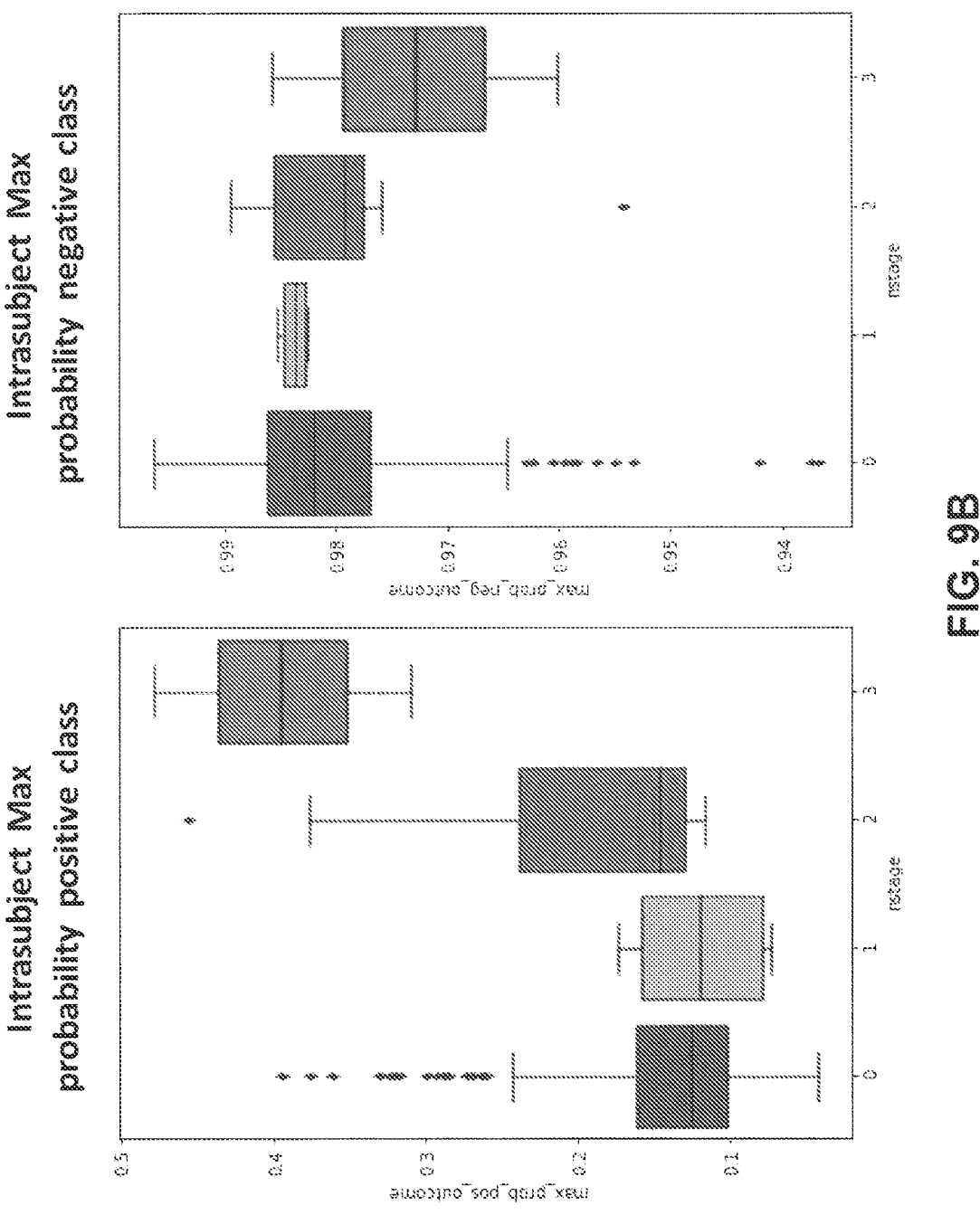

After training the step-up approach using a Random Forest Classifier, the subject level performance of the bootstrap model achieved a AUC=77.7%, Sensitivity=81.8%, and Specificity=59.9%, as illustrated in FIG. 9A. Thus, the performance of the two-step bootstrap model was an improvement in comparison to the approach described in Example 2. Similar performance was achieved using a LASSO Classifier. Finally, the model can be used to plot the distribution of scores (or max probabilities) across N stage (FIG. 9B). It is interesting to note that the model yields a higher max probability for those cases with higher N stage. This probability score could be used in different clinical contexts to enable different triage decision making tools.

Additional data for training and testing could provide a model that predicts N as a categorical rather than binary covariable.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, the above specification is not restrictive. It will be appreciated that various changes can be made without departing from the spirit and scope of the present disclosure(s). Many variations will become apparent to those skilled in the art upon review of this specification.

Example 4: Example Guided Interventions Using CT Image-Based Prediction Device

An image-based device that implements the methods described herein (e.g., deploying a risk model for predicting lymph node (LN) level risks of metastatic cancer for lymph nodes) will impact clinical care because of the poor performance of conventional methods, which involve PET scanning. A recent examination of 219 NSCLC patients who with systematic lymph node dissection/sampling examined the performance of pre-operative PET staging (e.g., Li et al., Implications of False Negative and False Positive Diagnosis in Lymph Node Staging of NSCLC by Means of 18F-FDG PET/CT. PLoS ONE 8(10):e78552, the entirety of which is incorporated by reference in its entirety). The sensitivity, specificity, PPV and NPV for PET for detecting hilar and mediastinal lymph node metastases was 74.2%, 54.4%, 86.8% and 73.5% with a false negative rate of 13.2% and false positive rate of 45.5%. Therefore, the methods described herein represent non-invasive techniques for detecting metastatic disease that has resulted in lymph node involvement, which will improve decision making and clinical care. Examples of the impact this device will have on decision making and clinical care include:

Prompt additional testing in subjects with tumors whose size is low risk for metastases. Since there is no standard of care for the use of pre-operative PET scanning or lymph node biopsy in those with small lung tumors, a prediction of lymph node involvement based on CT images captured by a CT device prompts subsequent testing via a PET scan or via bronchoscopic sampling of the subject's lymph nodes. In comparison, conventional methods would have directed the subject to surgery and in which more advanced disease stage would only be recognized intra-operatively.

Prompt tissue based sampling of lymph nodes in those that obtain a negative PET result. While there is a general awareness that PET has a false positive and false negative rate of failure, diagnostic testing is heavily influenced by the results of a PET scan. Patients with smaller tumor sizes and a negative PET often go onto surgery without additional LN sampling. This subset of patients would benefit from additional LN sampling prior to surgery.

Staging patients with false positive PET scans and demonstrate their eligibility for surgical intervention. Currently, patients who are strongly suspected of having advanced stage disease based upon a PET scan go onto non-curative systemic/non-surgical therapies without additional confirmatory LN sampling. A patient who receives a prediction of lymph node involvement (e.g., based on CT images of lymph nodes) and a negative PET result patient would instead go onto more definitive lymph node sampling prior to making a decision about surgery. Thus, these patients can be a candidate for surgical resection, and would increase their chances of cure.

Inform which LN is most likely to have metastatic disease. Patients at high risk for metastatic disease go onto bronchoscopic or surgical sampling of lymph nodes. Typically, this strategy places its strongest focus on those LN proximal to the tumor leaving more remote LN unsampled or under sampled. Here, methods described herein enable a prediction of lymph node involvement and furthermore, identification of the involved lymph node(s). This guides clinical teams to appropriately focus their sampling strategy to obtain tissue, maximize yield, and minimize the risk of missing a diagnosis.

Refine enrollment in clinical trials focused on patients without LN metastases. Patients with local disease are often sought for clinical trials focused on local delivery (transbronchial needle instillation of chemotherapy or ablation). Unfortunately, such patients are often found to have more advanced stage cancer during the procedure when undergoing lymph node sampling. This delays appropriate care. Thus, implementation of the methods described herein (e.g., deploying a risk model for predicting lymph node (LN) level risks of metastatic cancer for lymph nodes) enables identification of patients exhibiting lymph involvement and therefore, these patients need not be enrolled in clinical trials focused on patients without metastasis.

The invention claimed is:

1. A method of determining a subject level risk of metastatic cancer of a subject, the method comprising:
  obtaining one or more images captured from the subject comprising a plurality of lymph nodes of the subject; and
  predicting the subject level risk of metastatic cancer by applying a risk model to extracted features of the obtained one or more images, the risk model trained to predict lymph node (LN) level risks of metastatic cancer for lymph nodes in images,
  wherein the risk model is trained using at least labels derived from imputed LN-level risks of metastatic cancer for a set of lymph nodes of a reference individual, the imputed LN-level risks of the set of lymph nodes determined using at least an imputation model that discriminates between cancerous and non-cancerous lymph nodes of training images.

2. The method of claim 1, wherein predicting the subject level risk of metastatic cancer further comprises:
  selecting one or more of the plurality of lymph nodes based on their LN-level risk of metastatic cancer predicted by the risk model; and
  determining the subject level risk of metastatic cancer using the LN-level risk of metastatic cancer predicted for the one or more lymph nodes.

3. The method of claim 2, wherein selecting one or more of the plurality of lymph nodes comprises identifying the lymph node with a highest probability of LN-level risk, and wherein determining the subject level risk of metastatic cancer comprises assigning the highest probability of LN-level risk as the subject level risk of metastatic cancer.

4. The method of claim 1, wherein the risk model predicts LN-level risks of metastatic cancer with a greater range of probabilities than the than a range of probabilities of imputed LN-level risks predicted by the imputation model.

5. The method of claim 1, wherein the set of lymph nodes of a reference individual is selected by: determining a median risk value; and comparing imputed LN-level risks of the lymph nodes of the reference individual to the median risk value.

6. The method of claim 5, wherein the set of lymph nodes of a reference individual is further selected by:
  including one or more lymph nodes with LN-level risks greater than the median risk value in the set of lymph nodes.

7. The method of claim 5, wherein one or more lymph nodes with LN-level risks less than the median risk value in the set of lymph nodes are excluded from the set of lymph nodes.

8. The method of claim 5, wherein the median risk value is a median intrasubject LN-level risk of the reference individual.

9. The method of claim 5, wherein the one or more images comprises a computed tomography (CT) image.

10. The method of claim 1, wherein the one or more images comprises are obtained from a thoracic CT scan.

11. A method of training a risk model, the method comprising:
  applying an imputation model to generate imputed LN-level risks for a plurality of lymph nodes in training images;
  selecting a set of lymph nodes, wherein the lymph nodes in the set have LN-level risks that are greater than a median risk value; and
  using the LN-level risks of the lymph nodes in the set of lymph nodes as reference ground truths for training the risk model, the risk model predicting LN-level risks with a greater range of probabilities than a range of probabilities of imputed LN-level risks predicted by the imputation model.

12. The method of claim 11, wherein the risk model is further trained by extracting features from one or more radiomic panels; and training the risk model using at least the extracted features.

13. The method of claim 12, wherein extracting features from the one or more radiomic panels comprises:
  defining a region of interest (ROI) in the one or more radiomic panels, the defined ROI comprising a lymph node; and
  extracting features from the ROI in the one or more radiomic panels.

14. The method of claim 12, wherein the extracted features include one or more feature categories of first order features, shape features, gray level co-occurrence matrix 1 (GLCM) features, gray level run length matrix (GLRLM) features, gray level size zone matrix (GLSZM) features, and neighborhood gray tone difference matrix (NGTDM) features.

15. A system for determining a subject level risk of metastatic cancer of a subject, the system comprising:
  an imaging device configured to capture one or more images of the subject; and
  a computing device configured to perform the steps of:
    obtaining one or more images captured from the subject comprising a plurality of lymph nodes of the subject; and
    predicting the subject level risk of metastatic cancer by applying a risk model to extracted features of the obtained one or more images, the risk model trained to predict lymph node (LN) level risks of metastatic cancer for lymph nodes in images,
    wherein the risk model is trained using at least labels derived from imputed LN-level risks of metastatic cancer for a set of lymph nodes of a reference individual, the imputed LN-level risks of the set of lymph nodes determined using at least an imputation model that discriminates between cancerous and non-cancerous lymph nodes of training images.

16. The system of claim 15, wherein predicting the subject level risk of metastatic cancer further comprises:

selecting one or more of the plurality of lymph nodes based on their LN-level risk of metastatic cancer predicted by the risk model; and determining the subject level risk of metastatic cancer using the LN-level risk of metastatic cancer predicted for the one or more lymph nodes.

17. The system of claim 16, wherein selecting one or more of the plurality of lymph nodes comprises identifying the lymph node with a highest probability of LN-level risk, and wherein determining the subject level risk of metastatic cancer comprises assigning the highest probability of LN-level risk as the subject level risk of metastatic cancer.

18. The system of claim 15, wherein the risk model predicts LN-level risks of metastatic cancer with a greater range of probabilities than a range of probabilities of imputed LN-level risks predicted by the imputation model.

19. The system of claim 15, wherein the set of lymph nodes of a reference individual is selected by:

determining a median risk value; and comparing imputed LN-level risks of the lymph nodes of the reference individual to the median risk value.

20. The system of claim 19, wherein the set of lymph nodes of a reference individual is further selected by:

including one or more lymph nodes with LN-level risks greater than the median risk value in the set of lymph nodes.

* * * * *